(12) United States Patent
Yang et al.

(10) Patent No.: US 10,875,922 B2
(45) Date of Patent: Dec. 29, 2020

(54) ANTI-PDL1 ANTIBODY FORMULATIONS

(71) Applicant: Genentech, Inc., South San Francisco, CA (US)

(72) Inventors: Ying Yang, South San Francisco, CA (US); Sreedhara Alavattam, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 264 days.

(21) Appl. No.: 15/081,785

(22) Filed: Mar. 25, 2016

(65) Prior Publication Data

US 2016/0319022 A1 Nov. 3, 2016

Related U.S. Application Data

(63) Continuation of application No. PCT/US2014/057821, filed on Sep. 26, 2014.

(60) Provisional application No. 61/883,953, filed on Sep. 27, 2013.

(51) Int. Cl.
*A61K 39/395* (2006.01)
*C07K 16/28* (2006.01)
*A61K 39/00* (2006.01)

(52) U.S. Cl.
CPC .... *C07K 16/2827* (2013.01); *A61K 39/39591* (2013.01); *A61K 2039/505* (2013.01); *C07K 2317/41* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,675,187 A | 6/1987 | Konishi et al. | |
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,591,828 A | 1/1997 | Bosslet et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,075,181 A | 6/2000 | Kucherlapati et al. | |
| 6,150,584 A | 11/2000 | Kucherlapati et al. | |
| 6,919,436 B2 | 7/2005 | Lihme et al. | |
| 6,982,321 B2 | 1/2006 | Winter | |
| 7,078,492 B2 | 7/2006 | Pirofski et al. | |
| 7,087,409 B2 | 8/2006 | Barbas, III et al. | |
| 7,153,507 B2 | 12/2006 | Van de Winket et al. | |
| 7,189,826 B2 | 3/2007 | Rodman | |
| 8,217,149 B2 | 7/2012 | Irving et al. | |
| 8,372,396 B2 | 2/2013 | Andya et al. | |
| 2005/0026229 A1 | 3/2005 | Reiter et al. | |
| 2005/0100546 A1 | 5/2005 | Jakobovits et al. | |
| 2005/0176122 A1 | 8/2005 | Lihme et al. | |
| 2005/0287149 A1 | 12/2005 | Keler et al. | |
| 2006/0059575 A1 | 3/2006 | Kusunoki et al. | |
| 2006/0088523 A1 | 4/2006 | Andya et al. | |
| 2006/0183887 A1 | 8/2006 | Jakobovits et al. | |
| 2006/0258841 A1 | 11/2006 | Michl et al. | |
| 2010/0203056 A1 | 8/2010 | Irving | |
| 2012/0315645 A1 | 12/2012 | Kaur | |
| 2016/0222117 A1 | 8/2016 | Irving et al. | |

FOREIGN PATENT DOCUMENTS

| | | |
|---|---|---|
| EP | 0 404 097 B1 | 12/1990 |
| EP | 3049441 B1 | 11/2019 |
| JP | 2008-520551 A | 6/2008 |
| JP | 2012-511329 A | 5/2012 |
| WO | WO-1991/10741 A1 | 2/1991 |
| WO | WO-92/09690 A2 | 6/1992 |
| WO | WO-1993/01161 A1 | 1/1993 |
| WO | WO-96/07754 A1 | 3/1996 |
| WO | WO-1996/33735 A1 | 10/1996 |
| WO | WO-1996/34096 A1 | 10/1996 |
| WO | WO-1998/24893 A2 | 6/1998 |
| WO | WO-2006/044908 A2 | 4/2006 |
| WO | WO-2006/044908 A3 | 4/2006 |
| WO | WO-2010/077634 A1 | 7/2010 |
| WO | WO-2012/003470 A2 | 1/2012 |
| WO | WO-2013/019906 A1 | 2/2013 |
| WO | WO-2013/079174 A1 | 6/2013 |
| WO | WO-2013/093809 A1 | 6/2013 |
| WO | WO-2014/195852 A1 | 12/2014 |
| WO | WO-2015/112805 A1 | 7/2015 |

OTHER PUBLICATIONS

Amadzadeh et al. "Tumor Antigen-Specific CD8 T Cells Infiltrating the Tumor Express High Levels of PD-1 and are Functionally Impaired," *Blood* 114(8):1537-1544, (Aug. 2009).
Barbas et al. "Semisynthetic Combinatorial Antibody Libraries: A Chemical Solution to the Diversity Problem," *Proc. Natl. Acad. Sci. USA*, 89: 4457-4461, (May 1992).
Barbas et al. "Assembly of Combinatorial Antibody Libraries on Phage Surfaces: The Gene III Site," *Proc. Natl. Acad. Sci. USA*, 88: 7978-7982 (Sep. 1991).
Bass et al "Hormone Phage: An Enrichment Method for Variant Proteins With Altered Binding Properties," *Proteins* 8:309-314, (1990).
Boerner et al. "Production of Antigen-Specific Human Monoclonal Antibodies From in Vitro-Primed Human Splenocytes," *J. Immunol.* 147(1):86-95, (Jul. 1, 1991).
Bretscher et al. "A Theory of Self-Nonself Discrimination," *Science* 169:1042-1049 (1970).
Bretscher. "A Two-Step, Two-Signal Model for the Primary Activation of Precursor Helper T Cells," *Proc. Natl. Acad. Sci. USA*, 96:185-190, (Jan. 1999).

(Continued)

*Primary Examiner* — Yunsoo Kim
(74) *Attorney, Agent, or Firm* — Morrison & Foerster LLP

(57) ABSTRACT

The invention provides stable aqueous pharmaceutical formulations comprising an anti-PDL1 antibody. The invention also provides methods for making such formulations and methods of using such formulations.

31 Claims, 12 Drawing Sheets

Specification includes a Sequence Listing.

(56) References Cited

OTHER PUBLICATIONS

Brodeur et al. "Mouse-Human Myeloma Partners for the Production of Heterohybridomas," Chapter 4 in *Monoclonal Antibody Production Techniques and Applications*, Marcel Dekker, Inc. New York, New York, pp. 51-63 (1987).
Brüggemann et al. "Designer Mice: The Production of Human Antibody Repertoires in Transgenic Animals," *Year in Immunol.* 7:33-40, (1993).
Chothia et al. "Canonical Structures for the Hypervariable Regions of Immunoglobulins," *J. Mol. Biol.* 196:901-917, (1987).
Clackson et al. "Making Antibody Fragments Using Phage Display Libraries," *Nature* 352:624-628, (Aug. 15, 1991).
Cole et al. "The EBV-Hybridoma Technique and its Application to Human Lung Cancer," *Monoclonal Antibodies and Cancer Therapy*, Alan R. Liss, Inc., New York, New York, pp. 77-96, (1985).
Embleton et al. "In-Cell PCR From mRNA: Amplifying and Linking the Rearranged Immunoglobulin Heavy and Light Chain V-Genes Within Single Cells," *Nucl. Acids Res.* 20(15):3831-3837, (1992).
Even et al. "Serum-Free Hybridoma Culture: Ethical, Scientific and Safety Considerations," *Trends in Biotechnology*, 24(3):105-108, (Mar. 2006).
Fellouse et al. "Synthetic Antibodies From a Four-Amino-Acid Code: A Dominant Role for Tyrosine in Antigen Recognition," *Proc. Natl. Acad. Sci. USA* 101 (34):12467-12472, (Aug. 24, 2004).
Fishwild et al. "High-avidity human IgGK Monoclonal Antibodies from a Novel Strain of Minilocus Transgenic Mice," *Nature Biotechnol.* 14:845-851, (Jul. 1996).
Franek. "Oligopeptides as Tools for Improving Productivity of Hypbridoma Cells Cultures," Chapter VI in *Trends in Monoclonal Antibody Research*, Marie A. Simmons, ed., Nova Science Publishers, Inc. pp. 111-122, (2005).
Goding. "Production of Monoclonal Antibodies," Chapter 3 in *Monoclonal Antibodies: Principles and Practice*, Academic Press, pp. 59-103, (1983).
Gram et al. "In Vitro Selection and Affinity Maturation of Antibodies From a Naïve Combinatorial Immunoglobulin Library," *Proc. Natl. Acad. Sci USA*, 89:3576-3580, (Apr. 1992).
Griffiths et al. "Human Anti-Self Antibodies With High Specificity From Phage Display Libraries," *EMBO J.* 12(2):725-734, (1993).
Hamers-Casterman et al. "Naturally Occurring Antibodies Devoid of Light Chains," *Nature* 363:446-448, (Jun. 3, 1993).
Hammerling et al. "Production of Antibody-Producing Hybridomas in the Rodent System," Chapter 12, in *Monoclonal Antibodies and T-Cell Hybridomas*, Elsevier/North Holland Biomedical Press, New York, pp. 563-681, (1981).
Harris. "Therapeutic Monoclonal. Production of Humanized Monoclonal Antibodies for In Vivo Imaging and Therapy," *Biochem. Soc. Transactions* 23:1035-1038, (1995).
Hawkins et al. "Selection of Phage Antibodies by Binding Affinity. Mimicking Affinity Maturation," *J. Mol. Biol.* 226:889-896, (1992).
Hogrefe et al. "A Bacteriophage Lambda Vector for the Cloning and Expression of Immunoglobulin Fab Fragments on the Surface of Filamentous Phage," *Gene* 128:119-126, (1993).
Holliger et al. "Diabodies": Small Bivalent and Bispecific Antibody Fragments, *Proc. Natl. Acad. Sci. USA* 90:6444-6448, (Jul. 1993).
Hongo et al. "Development and Characterization of Murine Monoclonal Antibodies to the Latency-Associated Peptide of Transforming Growth Factor $\beta_1$," *Hybridoma* 14(3):253-260, (1995).
Hoogenboom et al. "By-Passing Immunisation. Human Antibodies From Synthetic Repertoires of Germline $V_H$ Gene Segments Rearranged in Vitro," *J. Mol. Biol.* 227:381-388, (1992).
Hoogenboom et al. "Overview of Antibody Phage-Display Technology and Its Applications," Chapter 1 in *Methods in Molecular Biology*, O'Brien et al., ed., Human Press, Totowa, New Jersey, 178:1-37, (2001).
Hoogenboom et al. "Multi-Subunit Proteins on the Surface of Filamentous Phage: Methodologies for Displaying Antibody (Fab) Heavy and Light Chains," *Nucl. Acids Res.* 19(15):4133-4137, (1991).
Hudson et al. "Engineered Antibodies," *Nat. Med.* 9(1):129-134, (Jan. 2003).
Hurle et al. "Protein Engineering Techniques for Antibody Humanization," *Curr. Op. Biotech.* 5:428-433, (1994).
Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555, (Mar. 1993).
Jakobovits et al. "Germ-Line Transmission and Expression of a Human-Derived Yeast Artificial Chromosome," *Nature* 362:255-258, (Mar. 18, 1993).
Jenkins et al. "Antigen Presentation by Chemically Modified Splenocytes Induces Antigen-Specific T Cell Unresponsiveness in Vitro and in Vivo," *J. Exp. Med.* 165:302-319, (Feb. 1987).
Johnson et al. "The Kabat Database and a Bioinformatics Example," Chapter 2 in *Methods in Molecular Biology*, Lo, B.K.C., ed., Human Press, Totowa, N.J., 248:1-25, (2003).
Jones et al. "Replacing the Complementarity-Determining Regions in a Human Antibody With Those From a Mouse," *Nature* 321:522-525, (May 29, 1986).
Jones et al. "Rapid PCR-Cloning of Full-Length Mouse Immunoglobulin Variable Regions," *Biotechnology.* 9:88-89, (Jan. 1991).
Jones. "Analysis of Polypeptides and Proteins," *Adv. Drug Delivery Rev.* 10:29-90, (1993).
Keir et al. "PD-1 and Its Ligands in Tolerance and Immunity," *Annu. Rev. Immunol.* 26:677-704, (2008, e-pub. Jan. 2, 2008).
Köhler et al. "Continuous Cultures of Fused Cells Secreting Antibody of Predefined Specificity," *Nature* 256:495-497, (Aug. 7, 1975).
Kozbor et al. "A Human Hybrid Myeloma for Production of Human Monoclonal Antibodies," *J. Immunol.* 133(6):3001-3005, (Dec. 1984).
Lafferty et al. "A New Analysis of Allogeneic Interactions," *Aust. J. Exp. Biol. Med. Sci.* 53(1):27-42, (Feb. 1975).
Lee et al. "High-affinity Human Antibodies From Phage-displayed Synthetic Fab Libraries With a Single Framework Scaffold," *J. Mol. Biol.* 340(5):1073-1093, (2004).
Lee et al. "Bivalent Antibody Phage Display Mimics Natural Immunoglobulin," *J. Immunol. Methods* 284(1-2):119-132, (2004).
Lenschow et al. "CD28/B7 System of T Cell Costimulation," *Ann. Rev. Immunol.* 14:233-258, (1996).
Leung et al. "A Method for Random Mutagenesis of a Defined DNA Segment Using a Modified Polymerase Chain Reaction," *Technique* 1(1):11-15, (Aug. 1989).
Li et al. Human Antibodies for Immunotherapy Development Generated Via a Human B Cell Hybridoma Technology, *Proc. Natl. Acad. Sci. USA* 103(10):3557-3562, (Mar. 7, 2006).
Lonberg et al. "Antigen-Specific Human Antibodies From Mice Comprising Four Distinct Genetic Modifications," *Nature* 368:856-859, (Apr. 28, 1994).
Lonberg et al. "Human Antibodies From Transgenic Mice," *Intern. Rev. Immunol.* 13:65-93, (1995).
Marks et al. "By-Passing Immunization. Human Antibodies From V-Gene Libraries Displayed on Phage," *J. Mol. Biol.* 222:581-597, (1992).
Marks et al. "By-Passing Immunization: Building High Affinity Human Antibodies by Chain Shuffling," *Bio/Technology* 10: 779-783, (Jul. 1992).
Matsuda et al. "Structure and Physical Map of 64 Variable Segments in the $3^1$ 0.8-Megabase Region of the Human Immunoglobulin Heavy-Chain Locus," *Nature Genet.* 3:88-94, (Jan. 1993).
Morrison. "Success in Specification," *Nature* 368:812-813, (Apr. 28, 1994).
Morrison et al. "Chimeric Human Antibody Molecules: Mouse Antigen-Binding Domains With Human Constant Region Domains," *Proc. Natl. Acad. Sci. USA* 81:6851-6855.
Munson et al. "Ligand: A Versatile Computerized Approach for Characterization of Ligand-Binding Systems," *Anal. Biochem.* 107:220-239, (1980).
Murakami et al. Cell Cycle Regulation, Oncogenes, and Antineoplastic Drugs, Chapter 1 in *The Molecular Basis of Cancer*, Mendelsohn and Israel, eds., (W.B. Saunders Company, Philadelphia, PA, pp. 3-16, (1995).

(56) References Cited

OTHER PUBLICATIONS

Neuberger. "Generating High-Avidity Human Mabs in Mice," *Nature Biotechnol.* 14:826, (Jul. 1996).
Ni. "Research Progress and Future Perspectives in Antibodomics and Antibodomic Drugs," *Xiandai Mianyixue* 26(4):265-268, (2006), (Translation of the Abstract 3 pages).
Nicolaou et al. "Calicheamicin 0 : A Rationally Designed Molecule with Extremely Potent and Selective DNA Cleaving Properties and Apoptosis Inducing Activity," *Angew. Chem. Intl. Ed. Engl.* 33(2):183-186, (1994).
Okazaki et al. "PD-1 and PD-1 Ligands: From Discovery to Clinical Application," *Intern. Immun.* 19(7):813-824.
Orlandi et al. "Cloning Immunoglobulin Variable Domains for Expression by the Polymerase Chain Reaction," *Proc. Natl. Acad. Sci. USA* 86:3833-3837, (May 1989).
Ørum et al. "Efficient Method for Constructing Comprehensive Murine Fab Antibody Libraries Display on Phage," *Nucleic Acids Res.* 21(19):4491-4498, (1993).
Pearlman et al. "Analysis of Protein Drugs," Chapter 6 in *Peptide and Protein Drug Delivery*, Vincent Lee ed., Marcel Dekker, Inc., New York, N.Y., pp. 247-301, (1991).
Plückthun. "Antibodies From *Escherichia coli*," Chapter 11 in *The Pharmacology of Monoclonal Antibodies*, Rosenburg and Moore eds., Springer-Verlag, New York, N.Y., pp. 269-315, (1994).
Plückthun. "Mono-and Bivalent Antibody Fragments Produced in *Escherichia coli*: Engineering, Folding and Antigen Binding," *Immunol. Rev.* 130:151-188, (1992).
Presta. "Antibody Engineering," *Curr. Op. Struct. Biol.* 2:593-596 (1992).
Riechmann et al. "Reshaping Human Antibodies for Therapy," *Nature* 332:323-327, (Mar. 24, 1988).
Sastry et al. "Cloning of the Immunological Repertoire in *Escherichia coil* for Generation of Monoclonal Catalytic Antibodies: Construction of a Heavy Chain Variable Region-Specific cDNA Library," *Proc. Natl. Acad. Sci. USA* 86:5728-5732, (Aug. 1989).
Sharpe et al. "The B7-CD28 Superfamily," Nat. Rev. 2:116-126, (Feb. 2002).
Sheriff et al. "Redefining the Minimal Antigen-Binding Fragment," *Nature Struct. Biol.* 3(9):733-736, (Sep. 1996).
Sidhu et al. "Phage-Displayed Antibody Libraries Synthetic Heavy Chain Complementarity Determining Regions," *J. Mol. Biol.* 338(2):299-310, (2004).
Skerra. "Bacterial Expression of Immunoglobulin Fragments," *Curr. Opinion in Immunol.* 5:256-262, (1993).
Thompson et al. "Tumor B7-H1 is Associated With Poor Prognosis in Renal Cell Carcinoma Patients With Long-Term Follow-up," *Cancer Res.* 66(7):3381-3385, (Apr. 1, 2006).
Tomlinson et al. "The Repertoire of Human Germline $V_H$ Sequences Reveals about Fifty Groups of $V_H$ Segments with Different Hypervariable Loops," *J. Mol. Biol.*, 227:776-798, (1992).
Van Dijk et al. "Human Antibodies as Next Generation Therapeutics," *Curr. Opin. Pharmacol.* 5:368-374, (2001).
Vaswani et al. "Humanized Antibodies as Potential Therapeutic Drugs," *Ann. Allergy, Asthma & Immunol.* 1:105-115, (Aug. 1998).
Verhoeyen et al. "Reshaping Human Antibodies: Grafting an Antilysozyme Activity," *Science* 239:1534-1536, (Mar. 25, 1988).
Vollmers et al. "The "Early Birds": Natural IgM Antibodies and Immune Surveillance," *Histology and Histopathology*, 20(3):927-937, (2005).
Vollmers et al. "Death by Stress: Natural IgM-Induced Apoptosis," *Methods and Findings in Experimental and Clinical Pharmacology* 27(3):185-191, (2005).
Ward et al. "Binding Activities of a Repertoire of Single Immunoglobulin Variable Domains Secreted From *Escherichia coli*," *Nature* 341:544-546, (Oct. 1, 1989).
Waterhouse et al. "Combinatorial Infection and in Vivo Recombination: a Strategy for Making Large Phage Antibody repertoires," *Nucl. Acids Res.*, 21(9):2265-2266, (1993).
Williams et al. "Cloning and Sequencing of Human Immunoglobulin $V_{\lambda 1}$ Gene Segments," *Eur. J. Immunol.* 23:1456-1461, (1993).
Winter et al. "Making Antibodies by Phage Display Technology," *Ann. Rev. Immunol.* 12:433-455, (1994).
Xu et al. "Diversity in the eCDR3 Region of $V_H$ is Sufficient for Most Antibody Specificities," *Immunity* 13:37-45, (Jul. 2000).
Zapata et al. "Engineering Linear $F(ab')_2$ Fragments for Efficient Production in *Escherichia coli* and Enhanced Antiproliferative Activity," *Protein Eng.* 8(10):1057-1062, (1995).
International Search Report dated Dec. 22, 2014, for PCT Patent Application No. PCT/US2014/057821, filed on Sep. 28, 2014, 5 pages.
Written Opinion dated Dec. 22, 2014, for PCT Patent Application No. PCT/US2014/057821, filed on Sep. 28, 2014, 5 pages.
Gokarn et al. "Self-Buffering Antibody Formulations," *Journal of Pharmaceutical Sciences* 97(8):3051-3066, (Aug. 2008).
Wang et al. "Antibody Structure, Instability, and Formulation," *Journal of Pharmaceutical Sciences* 96(1):1-26, (Jan. 2007).
Communication from the Examining Division at the European Patent Office dated Jun. 1, 2017, for European Patent Application 14784169.6, filed on Sep. 26, 2014, 6 pages.
Daugherty, A.L. et al. (Aug. 7, 2006, e-pub. May 22, 2006). "Formulation and Delivery Issues for Monoclonal Antibody Therapeutics," *Adv. Drug Deliv. Rev.* 58(5-6):686-706.
International Preliminary Report on Patentability of International Application No. PCT/US2014/057821, dated Mar. 29, 2016, filed on Sep. 26, 2014, 7 pages.

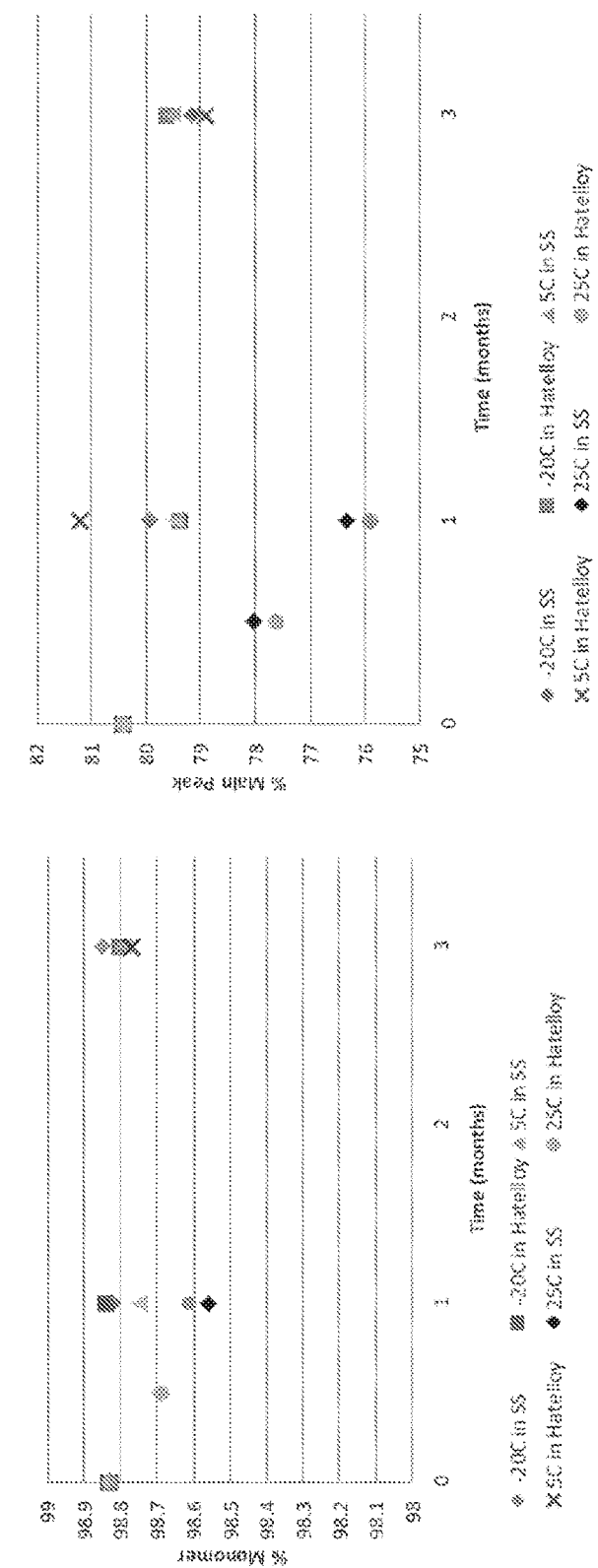

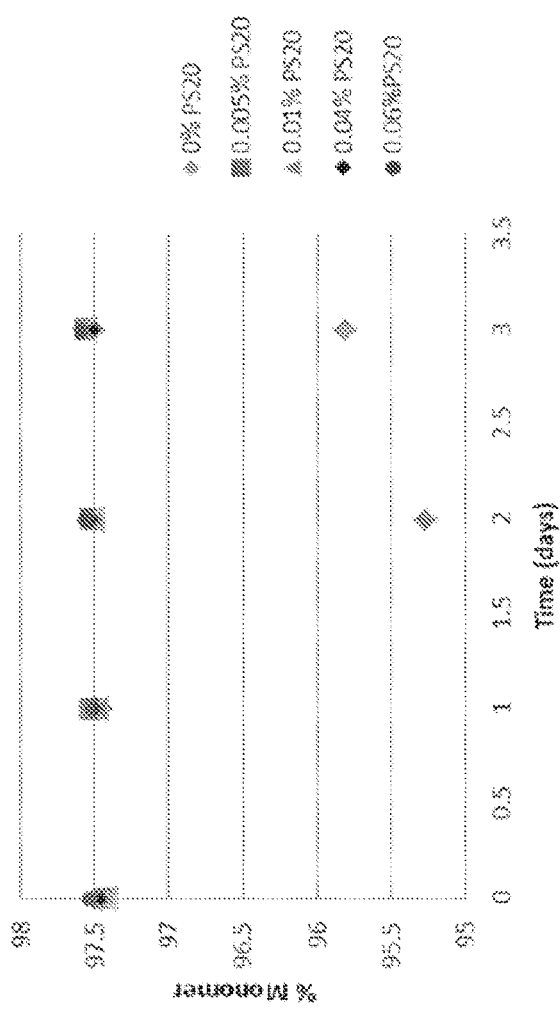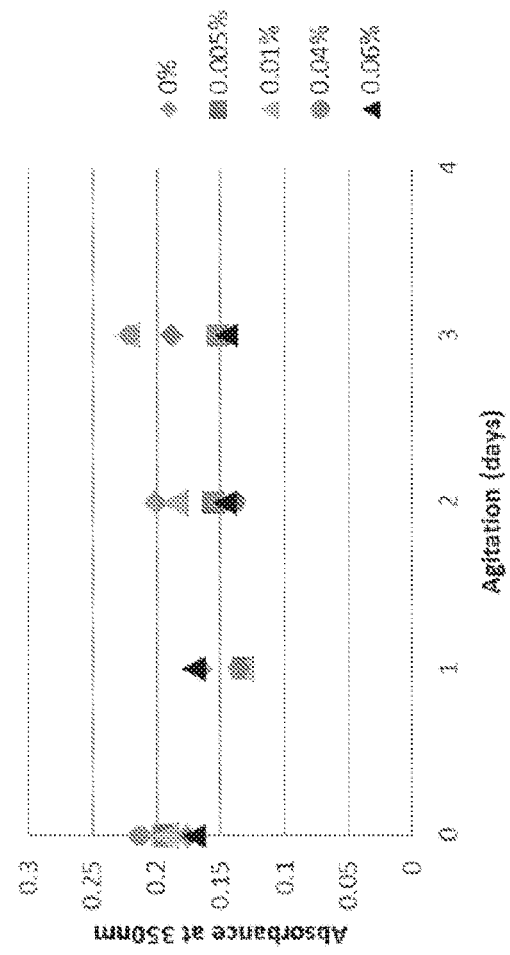
FIG. 9A
FIG. 9B

SEQUENCE LISTING

<160> NUMBER OF SEQ ID NOS: 36

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Arg Ala Ser Gln Asp Val Ser Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Gln Gln Tyr Leu Tyr His Pro Ala Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Phe Thr Phe Ser Asp Ser Trp Ile His
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

Ala Trp Ile Ser Pro Tyr Gly Gly Ser Thr Tyr Tyr Ala Asp Ser Val
1               5                   10                  15

Lys Gly

```
<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Arg His Trp Pro Gly Gly Phe Asp Tyr
1               5

<210> SEQ ID NO 7
<211> LENGTH: 108
<212> TYPE: PRT
<213> ORGANISM: Artificial Sequence
<220> FEATURE:
<223> OTHER INFORMATION: Synthetic Construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 8
<211> LENGTH: 122
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120
```

```
<210> SEQ ID NO 9
<211> LENGTH: 214
<212> TYPE: PRT
<213> ORGANISM: Artificial Sequence
<220> FEATURE:
<223> OTHER INFORMATION: Synthetic Construct

<400> SEQUENCE: 9
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 10
<211> LENGTH: 447
<212> TYPE: PRT
<213> ORGANISM: Artificial Sequence
<220> FEATURE:
<223> OTHER INFORMATION: Synthetic Construct

<400> SEQUENCE: 10
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ala Arg Arg His Trp Pro Gly Gly Phe Asp Tyr Trp Gly Gln Gly Thr
             100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = D or G

<400> SEQUENCE: 11
```

Gly Phe Thr Phe Ser Xaa Ser Trp Ile His
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = S or L
<220> FEATURE:
<221> NAME/KEY: VARIANT
<222> LOCATION: 10
<223> OTHER INFORMATION: Xaa = T or S

<400> SEQUENCE: 12

Ala Trp Ile Xaa Pro Tyr Gly Gly Ser Xaa Tyr Tyr Ala Asp Ser Val
1               5                   10                  15

Lys Gly

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Arg His Trp Pro Gly Gly Phe Asp Tyr
1               5

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Trp Val Arg Gln Ala Pro Gly Lys Gly Leu Glu Trp Val
1               5                   10

<210> SEQ ID NO 16
<211> LENGTH: 32
<212> TYPE: PRT
<213> ORGANISM: Artificial Sequence
<220> FEATURE:
<223> OTHER INFORMATION: Synthetic Construct

<400> SEQUENCE: 16

```
Arg Phe Thr Ile Ser Ala Asp Thr Ser Lys Asn Thr Ala Tyr Leu Gln
  1               5                  10                  15

Met Asn Ser Leu Arg Ala Glu Asp Thr Ala Val Tyr Tyr Cys Ala Arg
             20                  25                  30
```

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

```
Trp Gly Gln Gly Thr Leu Val Thr Val Ser Ala
  1               5                  10
```

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = D or V
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 7
<223> OTHER INFORMATION: Xaa = S or N
<220> FEATURE:
<221> NAME/KEY: VARIANT
<222> LOCATION: 9
<223> OTHER INFORMATION: Xaa = A or F
<220> FEATURE:
<221> NAME/KEY: VARIANT
<222> LOCATION: 10
<223> OTHER INFORMATION: Xaa = V or L

<400> SEQUENCE: 18

```
Arg Ala Ser Gln Xaa Xaa Xaa Thr Xaa Xaa Ala
  1               5                  10
```

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = F or T
<220> FEATURE:
<221> NAME/KEY: VARIANT
<222> LOCATION: 6
<223> OTHER INFORMATION: Xaa = Y or A

<400> SEQUENCE: 19

```
Ser Ala Ser Xaa Leu Xaa Ser
  1               5
```

<210> SEQ ID NO 20
<211> LENGTH: 9
<212> TYPE: PRT
<213> ORGANISM: Artificial Sequence
<220> FEATURE:

<223> OTHER INFORMATION: Synthetic Construct
<220> FEATURE:
<221> NAME/KEY: VARIANT
<222> LOCATION: 3
<223> OTHER INFORMATION: Xaa = Y, G, F, or S
<220> FEATURE:
<221> NAME/KEY: VARIANT
<222> LOCATION: 4
<223> OTHER INFORMATION: Xaa = L, Y, F or W
<220> FEATURE:
<221> NAME/KEY: VARIANT
<222> LOCATION: 5
<223> OTHER INFORMATION: Xaa = Y, N, A, T, G, F or I
<220> FEATURE:
<221> NAME/KEY: VARIANT
<222> LOCATION: 6
<223> OTHER INFORMATION: Xaa = H, V, P, T or I
<220> FEATURE:
<221> NAME/KEY: VARIANT
<222> LOCATION: 8
<223> OTHER INFORMATION: Xaa = A, W, R, P or T

<400> SEQUENCE: 20

Gln Gln Xaa Xaa Xaa Xaa Pro Xaa Thr
1               5

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Lys Ala Pro Lys Leu Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Phe Gly Gln Gly Thr Lys Val Glu Ile Lys Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Gly Phe Thr Phe Ser Asp Ser Trp Ile His
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic Construct

<400> SEQUENCE: 26

Ala Trp Ile Ser Pro Tyr Gly Gly Ser Thr Tyr Tyr Ala Asp Ser Val
1               5                   10                  15

Lys Gly

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Arg Ala Ser Gln Asp Val Ser Thr Ala Val Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Ser Ala Ser Phe Leu Tyr Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Gln Gln Tyr Leu Tyr His Pro Ala Thr
1               5

<210> SEQ ID NO 30
<211> LENGTH: 118
<212> TYPE: PRT
<213> ORGANISM: Artificial Sequence
<220> FEATURE:

<223> OTHER INFORMATION: Synthetic Construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 31
<211> LENGTH: 108
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 32
<211> LENGTH: 118
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val

```
                    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser
            115

<210> SEQ ID NO 33
<211> LENGTH: 11
<212> TYPE: PRT
<213> ORGANISM: Artificial Sequence
<220> FEATURE:
<223> OTHER INFORMATION: Synthetic Construct

<400> SEQUENCE: 33

Trp Gly Gln Gly Thr Leu Val Thr Val Ser Ser
 1               5                  10

<210> SEQ ID NO 34
<211> LENGTH: 30
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser
                20                  25                  30

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Trp Val Arg Gln Ala Pro Gly Lys Gly Leu Glu Trp Val Ala
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Phe Gly Gln Gly Thr Lys Val Glu Ile Lys
 1               5                  10
```

ANTI-PDL1 ANTIBODY FORMULATIONS

CROSS-REFERENCE TO RELATED APPLICATIONS

This application is a continuation of PCT/US2014/057821, filed Sep. 26, 2014, which claims the priority benefit of U.S. provisional application Ser. No. 61/883,953, filed Sep. 27, 2013, the disclosures of each of which is incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392022001SeqList.txt, date recorded: Mar. 25, 2016, size: 19 KB).

FIELD OF THE INVENTION

This invention relates to stable aqueous pharmaceutical formulations comprising anti-PDL1 antibodies.

BACKGROUND OF THE INVENTION

The provision of two distinct signals to T-cells is a widely accepted model for lymphocyte activation of resting T lymphocytes by antigen-presenting cells (APCs). Lafferty et al, Aust. J. Exp. Biol. Med. ScL 53: 27-42 (1975). This model further provides for the discrimination of self from non-self and immune tolerance. Bretscher et al, Science 169: 1042-1049 (1970); Bretscher, P. A., P.N.A.S. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., Ann. Rev. Immunol. 14:233 (1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

Therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. However, as an optimal therapeutic directed to a target in this pathway has yet to be commercialized, a significant unmet medical need exists.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY OF THE INVENTION

Provided herein are stable aqueous pharmaceutical formulations comprising an antibody. The formulation comprises an antibody (e.g., an anti-PDL1 antibody), a buffer, sucrose, and a surfactant, wherein the formulation has a pH of about 5.0 to about 7.0.

In one aspect, provided herein is a stable aqueous pharmaceutical formulation, the formulation comprising an anti-PDL1 monoclonal antibody in a concentration of about 40 mg/ml to about 125 mg/ml, histidine acetate or sodium acetate in a concentration of about 15 mM to about 25 mM, sucrose in a concentration of about 60 mM to about 240 mM, polysorbate in a concentration of about 0.005% (w/v) to about 0.06% (w/v), and pH about 5.0 to about 6.3.

In some embodiments, the monoclonal antibody in the formulation is about 40 mg/ml to about 80 mg/ml. In some embodiments, the monoclonal antibody in the formulation is about 54 mg/ml to about 66 mg/ml. In some embodiments, the monoclonal antibody in the formulation is about 60 mg/ml. In some embodiments, the monoclonal antibody in the formulation is about 60 mg/ml to about 125 mg/ml. In some embodiments, the monoclonal antibody in the formulation is about 125 mg/ml.

In some embodiments, said histidine acetate or sodium acetate in the formulation is in a concentration of about 17 mM to about 22 mM. In some embodiments, said histidine acetate or sodium acetate in the formulation is in a concentration of about 20 mM.

In some embodiments, said sucrose in the formulation is about 60 mM to about 180 mM. In some embodiments, said sucrose in the formulation is about 120 mM. In some embodiments, said sucrose in the formulation is about 240 mM.

In some embodiments, the formulation has a pH of about 5.5 to about 6.1. In some embodiments, the formulation has a pH of about 5.5 or about 5.8.

In some embodiments, said polysorbate in the formulation is polysorbate 20. In some embodiments, said polysorbate (e.g., polysorbate 20) in the formulation is about 0.02% to about 0.04%.

In some embodiments, said monoclonal antibody in the formulation is about 60 mg/ml, sucrose in the formulation is about 120 mM, and pH is about 5.8. In some embodiments, said monoclonal antibody in the formulation is about 125 mg/ml, sucrose in the formulation is about 240 mM, and pH is about 5.5.

In some embodiments, the formulation comprises a monoclonal antibody (e.g., an anti-PDL1 antibody described herein) in an amount of about 60 mg/mL, histidine acetate in a concentration of about 20 mM, sucrose in a concentration of about 120 mM, and polysorbate which is polysorbate 20 in a concentration of 0.04% (w/v), and the formulation has a pH of about 5.8.

In some embodiments, the formulation comprises a monoclonal antibody in an amount of about 125 mg/mL, histidine acetate in a concentration of about 20 mM, sucrose in a concentration of about 240 mM, and polysorbate which is polysorbate 20 in a concentration of 0.02%, and the formulation has a pH of about 5.5.

In some embodiments, said monoclonal antibody in the formulation is not subject to prior lyophilization. In some embodiments, said monoclonal antibody in the formulation is a full length antibody. In some embodiments, said monoclonal antibody in the formulation is an IgG1 antibody. In some embodiments, said monoclonal antibody in the formulation is a humanized antibody. In some embodiments, said monoclonal antibody in the formulation is an antibody fragment comprising an antigen-binding region. In some embodiments, the antibody fragment is a Fab or F(ab')$_2$ fragment.

In some embodiments, said monoclonal antibody in the formulation comprises
(a) a light chain variable region comprising:
  (1) HVR-L1 comprising the amino acid sequence RASQDVSTAVA (SEQ ID NO:1);
  (2) HVR-L2 comprising the amino acid sequence SASFLYS (SEQ ID NO:2);
  (3) HVR-L3 comprising the amino acid sequence QQYLYHPAT (SEQ ID NO:3); and
(b) a heavy chain variable region comprising:
  (1) HVR-H1 comprising the amino acid sequence GFTFSDSWIH (SEQ ID NO:4);
  (2) HVR-H2 comprising the amino acid sequence AWISPYGGSTYYADSVKG (SEQ ID NO:5);
  (3) HVR-H3 comprising the amino acid sequence RHWPGGFDY (SEQ ID NO:6).

In some embodiments, said monoclonal antibody in the formulation comprises a light chain variable region comprising the amino acid sequence of SEQ ID NO:7, and a heavy chain variable region comprising the amino acid sequence of SEQ ID NO:8. In some embodiments, said monoclonal antibody in the formulation comprises a light chain variable region having at least 85%, 86%, 87%, 88%, 89%, 90%, 91%, 92%, 93%, 94%, 95%, 96%, 97%, 98%, or 99% sequence identity to the light chain variable region having the amino acid sequence of SEQ ID NO:7, and a heavy chain variable region having at least 85%, 86%, 87%, 88%, 89%, 90%, 91%, 92%, 93%, 94%, 95%, 96%, 97%, 98%, or 99% identity to the heavy chain variable region having the amino acid sequence of SEQ ID NO:8. In some embodiments, said monoclonal antibody in the formulation comprises a light chain variable region comprising the amino acid sequence of SEQ ID NO:7, and a heavy chain variable region comprising the amino acid sequence of SEQ ID NO:32. In some embodiments, said monoclonal antibody in the formulation comprises a light chain variable region having at least 85%, 86%, 87%, 88%, 89%, 90%, 91%, 92%, 93%, 94%, 95%, 96%, 97%, 98%, or 99% sequence identity to the light chain variable region having the amino acid sequence of SEQ ID NO:7, and a heavy chain variable region having at least 85%, 86%, 87%, 88%, 89%, 90%, 91%, 92%, 93%, 94%, 95%, 96%, 97%, 98%, or 99% identity to the heavy chain variable region having the amino acid sequence of SEQ ID NO:32. In some embodiments, said monoclonal antibody in the formulation comprises a light chain comprising the amino acid sequence of SEQ ID NO:9, and a heavy comprising the amino acid sequence of SEQ ID NO: 10. In some embodiments, said monoclonal antibody in the formulation comprises a light chain having at least 85%, 86%, 87%, 88%, 89%, 90%, 91%, 92%, 93%, 94%, 95%, 96%, 97%, 98%, or 99% sequence identity to the light chain having the amino acid sequence of SEQ ID NO:9, and a heavy chain having at least 85%, 86%, 87%, 88%, 89%, 90%, 91%, 92%, 93%, 94%, 95%, 96%, 97%, 98%, or 99% identity to the heavy chain having the amino acid sequence of SEQ ID NO:10.

In some embodiments, the formulation comprising the antibody is stored in a glass vial or a metal alloy container. In some embodiments, the metal alloy is 316L stainless steel or hastelloy. In some embodiments, the formulation is stable at 2-8° C. for at least 6 months, at least 12 months, at least 18 months or at least 24 months. In some embodiments, the antibody in the formulation retains, after storage, at least about 75%, at least about 80%, at least about 85%, at least about 90% of the biological activity before storage. In some embodiments, the biological activity is measured by antibody binding to PD-L1.

In some embodiments, the formulation described herein is sterile. In some embodiments, the formulation described herein is suitable to be administered to a subject. In some embodiments, the formulation described herein is for intravenous (IV) administration.

In another aspect, provided herein is an article of manufacture or kit comprising a container holding any of the stable aqueous pharmaceutical formulation described above and herein. In some embodiments, the container is a glass vial or a metal alloy container. In some embodiments, the metal alloy is 316L stainless steel or hastelloy.

In another aspect, provided herein is a method of treating a disease or disorder in a subject comprising administering an effective amount of the formulation described herein to the subject, wherein the disease or disorder is selected from the group consisting of infection, cancer, and inflammatory disease.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A) Average main peak rate loss from fractional factorial design of experiments (DOE). FIG. 1B) Main peak analysis from fractional factorial DOE. Main peak contains α-PDL1 charged species with the same pH as the pI (isoelectric point) of the molecule.

FIG. 2A) Average main peak rate loss from fractional factorial design of experiments (DOE). FIG. 2B) Main peak analysis from fractional factorial DOE. Main peak contains α-PDL1 charged species with the same pH as the pI (isoelectric point) of the molecule.

FIG. 3A) Average main peak rate loss from fractional factorial design of experiments (DOE). FIG. 3B) Main peak analysis from fractional factorial DOE. Main peak contains α-PDL1 monomer.

FIG. 4A) Average main peak rate loss from fractional factorial design of experiments (DOE). FIG. 4B) Main peak analysis from fractional factorial DOE. Main peak contains α-PDL1 monomer.

FIG. 6A) Graph of percent (%) monomer in formulations after five freeze thaw cycles during storage at −20° C. for the indicated time. FIG. 6B) Graph of percent (%) monomer in formulations stored at 5° C. for the indicated time. FIG. 6C) Graph of percent (%) main peak obtained from formulation after five freeze thaw cycles during storage at −20° C. for the indicated time. FIG. 6D) Graph of percent (%) main peak obtained from formulation stored at 5° C. for the indicated time.

FIG. 7A and FIG. 7B are a series of graphs showing stability of an α-PDL1 formulation after three freeze thaw cycles and storage in a stainless steel or hastelloy minican. FIG. 7A) Graph of percent (%) monomer in the formulation after storage at the indicated temperature for 3 months. FIG. 7B) Graph of percent (%) main peak in the formulation after storage at the indicated temperature for 3 months.

FIG. 8A) Graph of percent (%) monomer in the formulation after storage at the indicated temperature for 3 months. FIG. 8B) Graph of percent (%) main peak in the formulation after storage at the indicated temperature for 3 months.

FIG. 9A and FIG. 9B are a series of graphs showing stability of α-PDL1 formulations containing various concentration of PS20 when agitated in glass vials. FIG. 9A) Graph of percent (%) monomer in formulations after agitation for the indicated time at room temperature. FIG. 9B) Graph of turbidity as measured by absorbance at 350 nm after agitation for the indicated time at room temperature.

FIG. 11A) Graph of percent (%) monomer loss per week in the formulation after storage at 40° C. FIG. 11B) Graph of percent (%) main peak loss per week in the formulation after storage at 40° C.

DETAILED DESCRIPTION

I. Definitions

Figure 1A:
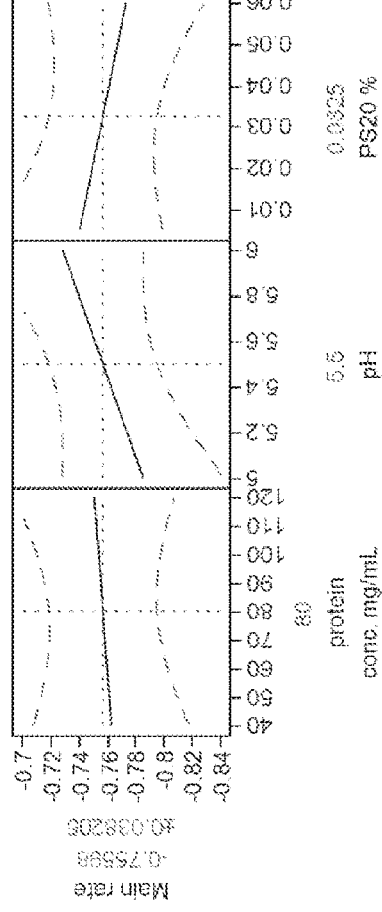
FIG. 1A and FIG. 1B are a series of graphs showing statistical analysis of stability data α-PDL1 formulations at 40° C. by ICIEF using JMP software.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

A "frozen" formulation is one at a temperature below 0° C. Generally, the frozen formulation is not freeze-dried, nor is it subjected to prior, or subsequent, lyophilization. In certain embodiments, the frozen formulation comprises frozen drug substance for storage (in stainless steel tank) or frozen drug product (in final vial configuration).

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301. Vincent Lee Ed., Marcel Dekker, Inc., New York, N.Y., Pubs. (1991) and Jones. A. *Adv. Drug Delivery Rev.* 10:

29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example.

An antibody "retains its biological activity" in a pharmaceutical formulation, if the biological activity of the antibody at a given time is at least about 60% (within the errors of the assay) of the biological activity exhibited at the time the pharmaceutical formulation was prepared as determined in an assay (e.g., an antigen binding assay). Other "biological activity" assays for antibodies are elaborated herein below.

As used herein, "biological activity" of a monoclonal antibody includes the ability of the antibody to bind to antigen and resulting in a measurable biological response which can be measured in vitro or in vivo.

A "deamidated" monoclonal antibody herein is one in which one or more asparagine residue thereof has been derivatized, e.g. to an aspartic acid or an iso-aspartic acid.

An "oxidized" monoclonal antibody herein is one in which one or more tryptophan residue and/or one or more methionine thereof has been oxidized.

A "glycated" monoclonal antibody herein is one in which one or more lysine residue thereof has been glycated.

An antibody which is "susceptible to deamidation" is one comprising one or more residue, which has been found to be prone to deamidate.

An antibody which is "susceptible to oxidation" is one comprising one or more residue, which has been found to be prone to oxidize.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, oxidation, aggregation, or fragmentation" is intended preventing or decreasing the amount of deamidation, oxidation, aggregation, or fragmentation relative to the monoclonal antibody formulated in a different formulation.

The antibody which is formulated is preferably essentially pure and desirably essentially homogeneous (e.g., free from contaminating proteins etc.). "Essentially pure" antibody means a composition comprising at least about 90% by weight of the antibody, based on total weight of proteins in the composition, preferably at least about 95% by weight. "Essentially homogeneous" antibody means a composition comprising at least about 99% by weight of antibody, based on total weight of proteins in the composition.

By "isotonic" is meant that the formulation of interest has essentially the same osmotic pressure as human blood. Isotonic formulations generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 4.5 to about 7.0, preferably from about 5.6 to about 7.0, for example from 5.6 to 6.9, 5.7 to 6.8, 5.8 to 6.7, 5.9 to 6.6, 5.9 to 6.5, 6.0, 6.0 to 6.4, or 6.1 to 6.3. In one embodiment the buffer has a pH 5.6, 5.7, 5.8, 5.9, 6.0, 6.1, 6.2, 6.3, 6.4, 6.5, 6.6, 6.7, 6.8, 6.9, or 7.0. For example, sodium phosphate is an example of buffers that will control the pH in this range.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20.

In a pharmacological sense, in the context of the invention, a "therapeutically effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predispose the mammal to the disorder in question.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al., *Angew. Chem Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds. The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders. Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', $F(ab\infty)_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988): Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see. e.g., U.S. Pat. No. 4,816,567; and Morrison et al., Proc. Natl. Acad. Sci. USA 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived firm non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel. Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see. e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1\times10^7$ M, preferably no more than about $1\times10^{-8}$ M and preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (20001; Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest,* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng.* 8(10): 1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≥10 nM, ≤1 nM, or ≤0.1 nM. In certain embodiments, an antibody specifically binds to an epitope on a protein that is conserved among the protein from different species. In another embodiment, specific binding can include, but does not require exclusive binding.

II. Antibody Formulations and Preparation

The invention herein relates to stable aqueous formulations comprising an antibody, such as an anti-PDL1 antibody. In some embodiments, the formulation comprises an antibody (e.g., a monoclonal antibody), sucrose, a buffer, and a surfactant, wherein the formulation has a pH of about 5.0 to about 7.0. In some embodiments, the antibody (e.g., an anti-PDL1 antibody described herein) in the formulation is in an amount of about 40 mg/ml to about 125 mg/ml. In some embodiments, the buffer is histidine (e.g., histidine acetate) or sodium acetate. In some embodiments, the buffer in the formulation is in a concentration of about 15 mM to about 25 mM. In some embodiments, sucrose in the formulation is about 60 mM to about 240 mM. In some embodiments, the surfactant in the formulation is polysorbate (e.g, polysorbate 20). In some embodiments, polysorbate in the formulation is in a concentration of about 0.005% (w/v) to about 0.06% (w/v). In some embodiments, the formulation has a pH of about 5.0 to about 6.3. In some embodiments, provided herein is stable aqueous pharmaceutical formulation, the formulation comprising an anti-PDL1 monoclonal antibody in a concentration of about 40 mg/ml to about 125 mg/ml, histidine acetate or sodium acetate in a concentration of about 15 mM to about 25 mM, sucrose in a concentration of about 60 mM to about 240 mM, polysorbate in a concentration of about 0.005% (w/v) to about 0.06% (w/v), and pH about 5.0 to about 6.3. In some embodiments, the formulation comprises an anti-PDL1 monoclonal antibody in amount of about 125 mg/ml, sucrose in a concentration of about 240 mM, and pH of about 5.5. In some embodiments, the formulation comprises an anti-PDL1 monoclonal antibody in amount of about 60 mg/ml, sucrose in a concentration of about 120 mM, and pH of about 5.8.

In some embodiments, the antibody in the formulation is stable at −20° C. for at least about 6 months, at least about 12 months, at least about 18 months, at least two years, at least three years, or at least four years. In some embodiments, the antibody in the formulation is stable at 2-8° C. for at least about 6 months, at least about 12 months, at least about 18 months, at least two years, or at least three years. In some embodiments, after storage, the antibody retains at least about 60%, at least about 65%, at least about 70%, at least about 75%, at least about 80%, at least about 85%, at least about 90%, or at least about 95% of its biological activity (e.g., binding to the target, or therapeutic potency exhibited before storage, i.e., at the time the pharmaceutical formulation was prepared.

In certain embodiments, the formulation is stable at about 40° C. for at least about 1, 2, 3, 4, 5, 6, 7, 14, 21, 28, or more days. In certain embodiments, the formulation is stable at about 40° C. for at least about 1, 2, 3, 4, 5, 6, 7, 8, or more weeks. In certain embodiments, the formulation is stable at about 25° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about 5° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, the formulation is stable at 5° C. or −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. Furthermore, the formulation is preferably stable following freezing (to, e.g., −20° C., −40° C. or −70° C.) and thawing of the formulation, for example following 1, 2, 3, 4, or 5 cycles of freezing and thawing.

A. Antibodies (Such as Anti-PDL1 Antibodies)

In some embodiments, the antibody in the formulation comprises at least one tryptophan (e.g., at least two, at least three, or at least four) in the heavy and/or light chain sequence. In some embodiments, amino acid tryptophan is in the CDR regions, framework regions and/or constant regions of the antibody. In some embodiments, the antibody comprises two or three tryptophan residues in the CDR regions. In some embodiments, the antibody in the formulation is an anti-PDL1 antibody. PDL1 (programmed cell death 1 ligand 1), also known as PDL1, B7-H1, B7-4, CD274, and B7-H, is a transmembrane protein, and its interaction with PD-1 inhibits T-cell activation and cytokine production. In some embodiments, the anti-PDL1 antibody described herein binds to human PD-L1. Examples of anti-PDL1 antibodies that can be formulated using the formulations described herein are described in PCT patent application WO 2010/077634 A1 and U.S. Pat. No. 8,217,149, which are incorporated herein by reference.

In some embodiments, the anti-PDL1 antibody is capable of inhibiting binding between PD-L1 and PD-1 and/or between PD-L1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and (Fab')$_2$ fragments. In some embodiments, the anti-PDL1 antibody is a humanized antibody. In some embodiments, the anti-PDL1 antibody is a human antibody.

Anti-PDL1 antibodies described in WO 2010/077634 A1 and U.S. Pat. No. 8,217,149 may be formulated in the formulations described herein. In some embodiments, the anti-PDL1 antibody comprises a heavy chain variable region comprising the amino acid sequence of SEQ ID NO:30 and a light chain variable region comprising the amino acid sequence of SEQ ID NO:31.

In one embodiment, the anti-PDL1 antibody comprises a heavy chain variable region polypeptide comprising an HVR-H1, HVR-H2 and HVR-H3 sequence, wherein:

```
                                          (SEQ ID NO: 11)
(a) the HVR-H1 sequence is GFTFSX₁SWIH;

(SEQ ID NO: 12)
(b) the HVR-H2 sequence is AWIX₂PYGGSX₃YYADSVKG;

(SEQ ID NO: 13)
(c) the HVR-H3 sequence is RHWPGGFDY;
``` further wherein: $X_1$ is D or G; $X_2$ is S or L; $X_3$ is T or S.

In one specific aspect, $X_1$ is D; $X_2$ is S and $X_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
                                          (SEQ ID NO: 14)
    HC-FR1 is EVQLVESGGGLVQPGGSLRLSCAAS (SEQ ID NO: 15)
    HC-FR2 is WVRQAPGKGLEWV (SEQ ID NO: 16)
    HC-FR3 is RFTISADTSKNTAYLQMNSLRAEDTAVYYCAR (SEQ ID NO: 17)
    HC-FR4 is WGQGTLVTVSA.
```

In a still further aspect, the heavy chain polypeptide is further combined with a variable region light chain comprising an HVR-L1, HVR-L2 and HVR-L3, wherein:

```
                                          (SEQ ID NO: 18)
(a) the HVR-L1 sequence is RASQX₄X₅X₆TX₇X₈A;

(SEQ ID NO: 19)
(b) the HVR-L2 sequence is SASX₉LX₁₀S,;

(SEQ ID NO: 20)
(c) the HVR-L3 sequence is QQX₁₁X₁₂X₁₃X₁₄PX₁₅T;
``` further wherein: $X_4$ is D or V; $X_5$ is V or I; $X_6$ is S or N; $X_7$ is A or F; $X_8$ is V or L; $X_9$ is F or T; $X_{10}$ is Y or A;

$X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
                                      (SEQ ID NO: 21)
LC-FR1 is DIQMTQSPSSLSASVGDRVTITC (SEQ ID NO: 22)
LC-FR2 is WYQQKPGKAPKLLIY (SEQ ID NO: 23)
LC-FR3 is GVPSRFSGSGSGTDFTLTISSLQPEDFATYYC (SEQ ID NO: 24)
LC-FR4 is FGQGTKVEIKR.
```

In another embodiment, provided is an isolated anti-PDL1 antibody or antigen binding fragment comprising a heavy chain and a light chain variable region sequence, wherein:
(a) the heavy chain comprises and HVR-H1, HVR-H2 and HVR-H3, wherein further:
  (i) the HVR-H1 sequence is GFTFSX$_1$SWIH; (SEQ ID NO: 11)
  (ii) the HVR-H2 sequence is AWIX$_2$PYGGSX$_1$YYADSVKG (SEQ ID NO:12)
  (iii) the HVR-H3 sequence is RHWPGGFDY, and (SEQ ID NO:13)
(b) the light chain comprises and HVR-L1, HVR-L2 and HVR-L3, wherein further
  (i) the HVR-L1 sequence is RASQX$_4$X$_5$X$_6$TX$_7$X$_8$A (SEQ ID NO:18)
  (ii) the HVR-L2 sequence is SASX$_9$LX$_{10}$S; and (SEQ ID NO:19)
  (iii) the HVR-L3 sequence is QQX$_{11}$X$_{12}$X$_{13}$X$_{14}$PX$_{15}$T; (SEQ ID NO:20)
Further wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup II consensus framework. In a still further aspect, one or more of the heavy chain framework sequences is the following:

```
HC-FR1
                                      (SEQ ID NO: 14)
EVQLVESGGGLVQPGGSLRLSCAAS

HC-FR2
                                      (SEQ ID NO: 15)
WVRQAPGKGLEWV

HC-FR3
                                      (SEQ ID NO: 16)
RFTISADTSKNTAYLQMNSLRAEDTAVYYCAR

HC-FR4
                                      (SEQ ID NO: 17)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                      (SEQ ID NO: 21)
DIQMTQSPSSLSASVGDRVTITC

LC-FR2
                                      (SEQ ID NO: 22)
WYQQKPGKAPKLLIY

LC-FR3
                                      (SEQ ID NO: 23)
GVPSRFSGSGSGTDFTLTISSLQPEDFATYYC

LC-FR4
                                      (SEQ ID NO: 24)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PDL1 antibody comprising a heavy chain and a light chain variable region sequence, wherein:
(a) the heavy chain further comprises and HVR-H1, HVR-H2 and an HVR-H3 sequence having at least 85% sequence identity to GFTFSDSWIH (SEQ ID NO:25), AWISPYGGSTYYADSVKG (SEQ ID NO:26) and RHWPGGFDY (SEQ ID NO:13), respectively, or
(b) the light chain further comprises an HVR-L1, HVR-L2 and an HVR-L3 sequence having at least 85% sequence identity to RASQDVSTAVA (SEQ ID NO:27). SASFLYS (SEQ ID NO:28) and QQYLYH-PAT (SEQ ID NO:29), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 14)
EVQLVESGGGLVQPGGSLRLSCAAS

HC-FR2
                                        (SEQ ID NO: 15)
WVRQAPGKGLEWV

HC-FR3
                                        (SEQ ID NO: 16)
RFTISADTSKNTAYLQMNSLRAEDTAVYYCAR

HC-FR4
                                        (SEQ ID NO: 17)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                        (SEQ ID NO: 21)
DIQMTQSPSSLSASVGDRVTITC

LC-FR2
                                        (SEQ ID NO: 22)
WYQQKPGKAPKLLIY

LC-FR3
                                        (SEQ ID NO: 23)
GVPSRFSGSGSGTDFTLTISSLQPEDFATYYC

LC-FR4
                                        (SEQ ID NO: 24)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PDL1 antibody comprising a heavy chain and a light chain variable region sequence, wherein:
(a) the heavy chain sequence has at least 85% sequence identity to the heavy chain sequence: EVQLVESGG-GLVQPGGSLRLSCAASGFTFSD-SWIHWVRQAPGKGLEWVAWIS PYGGSTYY-ADSVKGRFTISADTSKNTAYLQMNSLRA EDTAVYYCARRHWPGGFDY WGQGTLVTVSA (SEQ ID NO:30), or
(b) the light chain sequences has at least 85% sequence identity to the light chain sequence: DIQMTQSPSSL-SASVGDRVTITCRASQDVSTA-VAWYQQKPGKAPKLLIY SASF LYSGVPSRFSGSGSGTDFTLTISSLQPEDFA-TYYCQQYLYHPATFGQGTKVEIKR (SEQ ID NO:31).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 14)
EVQLVESGGGLVQPGGSLRLSCAAS

HC-FR2
                                        (SEQ ID NO: 15)
WVRQAPGKGLEWV

HC-FR3
                                        (SEQ ID NO: 16)
RFTISADTSKNTAYLQMNSLRAEDTAVYYCAR

HC-FR4
                                        (SEQ ID NO: 17)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                        (SEQ ID NO: 21)
DIQMTQSPSSLSASVGDRVTITC

LC-FR2
                                        (SEQ ID NO: 22)
WYQQKPGKAPKLLIY
```

```
LC-FR3
                                        (SEQ ID NO: 23)
GVPSRFSGSGSGTDFTLTISSLQPEDFATYYC

LC-FR4
                                        (SEQ ID NO: 24)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PDL1 antibody comprising a heavy chain and a light chain variable region sequence, wherein:
  (a) the heavy chain sequence has at least 85% sequence identity to the heavy chain sequence: EVQLVESGG-GLVQPGGSLRLSCAASGFFSD-SWIHWVRQAPGKGLEWVA WISPYGGSTYY-ADSVKGRFTISADTSKNTAYLQMNSLRAED TAVYYCARRHWPGGF DYWGQGTIVTVSS (SEQ ID NO:32), or
  (b) the light chain sequences has at least 85% sequence identity to the light chain sequence: DIQMTQSPSSL-SASVGDRVTITCRASQDVSTA-VAWYQQKPGKAPKLLIY SASF LYSGVPSRFSGSGSGTDFTLTISSLQPEDFA-TYYCQQYLYHPATFGQGTKVEIKR (SEQ ID NO:31).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VII subgroup III consensus framework. In a still further aspect, one or more of the heavy chain framework sequences is the following:

```
HC-FR1
                                        (SEQ ID NO: 14)
EVQLVESGGGLVQPGGSLRLSCAAS

HC-FR2
                                        (SEQ ID NO: 15)
WVRQAPGKGLEWV
```

```
HC-FR3
                                        (SEQ ID NO: 16)
RFTISADTSKNTAYLQMNSLRAEDTAVYYCAR

HC-FR4
                                        (SEQ ID NO: 33)
WGQGTLVTVSS,
```

In a still further aspect, the light chain framework sequences are derived from a Kabat kappa I, II, or IV subgroup sequence. In a still further aspect, the light chain framework sequences are VL kappa I consensus framework. In a still further aspect, one or more of the light chain framework sequences is the following:

```
LC-FR1
                                        (SEQ ID NO: 21)
DIQMTQSPSSLSASVGDRVTITC

LC-FR2
                                        (SEQ ID NO: 22)
WYQQKPGKAPKLLIY

LC-FR3
                                        (SEQ ID NO: 23)
GVPSRFSGSGSGTDFTLTISSLQPEDFATYYC

LC-FR4
                                        (SEQ ID NO: 24)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 34)
EVQLVESGGGLVQPGGSLRLSCAASGFTFS

HC-FR2
                                        (SEQ ID NO: 35)
WVRQAPGKGLEWVA
```

```
HC-FR3
                                                (SEQ ID NO: 16)
RFTISADTSKNTAYLQMNSLRAEDTAVYYCAR

HC-FR4
                                                (SEQ ID NO: 33)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                                (SEQ ID NO: 21)
DIQMTQSPSSLSASVGDRVTITC

LC-FR2
                                                (SEQ ID NO: 22)
WYQQKPGKAPKLLIY

LC-FR3
                                                (SEQ ID NO: 23)
GVPSRFSGSGSGTDFTLTISSLQPEDFATYYC

LC-FR4
                                                (SEQ ID NO: 36)
FGQGTKVEIK.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PDL1 antibody comprising a heavy chain and a light chain variable region sequence, wherein:
(c) the heavy chain further comprises and HVR-H1, HVR-H2 and an HVR-H3 sequence having at least 85% sequence identity to GFTFSDSWIH (SEQ ID NO:4), AWISPYGGSTYYADSVKG (SEQ ID NO:5) and RHWPGGFDY (SEQ ID NO:6), respectively, or
(d) the light chain further comprises an HVR-L1, HVR-L2 and an HVR-L3 sequence having at least 85% sequence identity to RASQDVSTAVA (SEQ ID NO:1), SASFLYS (SEQ ID NO:2) and QQYLYHPAT (SEQ ID NO:3), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                                (SEQ ID NO: 34)
EVQLVESGGGLVQPGGSLRLSCAAS

HC-FR2
                                                (SEQ ID NO: 35)
WVRQAPGKGLEWV

HC-FR3
                                                (SEQ ID NO: 16)
RFTISADTSKNTAYLQMNSLRAEDTAVYYCAR

HC-FR4
                                                (SEQ ID NO: 33)
WGQGTLVTVSSASTK.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                                (SEQ ID NO: 21)
DIQMTQSPSSLSASVGDRVTITC

LC-FR2
                                                (SEQ ID NO: 22)
WYQQKPGKAPKLLIY

LC-FR3
                                                (SEQ ID NO: 23)
GVPSRFSGSGSGTDFTLTISSLQPEDFATYYC

LC-FR4
                                                (SEQ ID NO: 24)
FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PDL1 antibody comprising a heavy chain and a light chain variable region sequence, wherein:
(a) the heavy chain sequence has at least 85% sequence identity to the heavy chain sequence: EVQLVESGG-GLVQPGGSLRLSCAASGFTFSD-SWIHWVRQAPGKGLEWVAWI SPYGGSTYY-ADSVKGRFTISADTSKNTAYLQMNSLRAED TAVYYCARRHWPGGFD YWGQGTLVTVSSASTK (SEQ ID NO:8), or (b) the light chain sequences has at least 85% sequence identity to the light chain sequence: DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKR (SEQ ID NO:7).

In some embodiments, provided is an isolated anti-PDL1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:7. In some embodiments, provided is an isolated anti-PDL1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:8. In some embodiments, provided is an isolated anti-PDL1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:7 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:8.

In a still further embodiment, provided is an isolated anti-PDL1 antibody comprising a heavy chain and a light chain sequence, wherein:
(a) the heavy chain sequence has at least 85% sequence identity to the heavy chain sequence: EVQLVESGGGLVQPGGSLRLSCAASGFTFSDSWIHWVRQAPGKGLEWVAWISPYGG STYYADSVKGRFTISADTSKNTAYLQMNSLRAEDTAVYYCARRHWPGGFDYWGQG TLVTVSSASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVV DVSHEDPEVKFNWYVDGV EVHNAKTKPREEQYASTYRVVSVLTVLHQDWLNGKEYKCKV SNKALPAPIEKTISK AKGQPREPQVYTLPPSREEMTKNQVSLTCLVKGFYPSDIAVEWESNGQPENNYKTTP PVLDSIXDSFFLYSKLTVDKSRWQQGNVFSCSVMHEALHNHYTQK SLSLSPG (SEQ ID NO:10), or
(b) the light chain sequences has at least 85% sequence identity to the light chain sequence: DIQMTQSPSSLSASVGDRVTITCRASQDVSTAVAWYQQKPGKAPKLLIYSASFLYSG VPSRFSGSGSGTDFTLTISSLQPEDFATYYCQQYLYHPATFCGQGTKVEIKRTVAAPSV FIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC (SEQ ID NO:9).

In some embodiments, provided is an isolated anti-PDL1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:9. In some embodiments, provided is an isolated anti-PDL1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 10. In some embodiments, provided is an isolated anti-PDL1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:9 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:10.

In some embodiments, the isolated anti-PDL1 antibody is an oxidized monoclonal antibody. In some embodiments, the oxidized monoclonal antibody in the formulation comprises a light chain comprising the amino acid sequence of SEQ ID NO:9, and a heavy comprising the amino acid sequence of SEQ ID NO:10. In some embodiments, the oxidized monoclonal antibody in the formulation comprises a heavy chain comprising the amino acid sequence of SEQ ID NO:10, wherein one or more of W33, W50, or W101 is oxidized. In some embodiments, the oxidized monoclonal antibody in the formulation comprises a heavy chain comprising the amino acid sequence of SEQ ID NO:10, wherein one or more of M253 and M429 is oxidized. In some embodiments, the oxidized monoclonal antibody retains at least about 60%, at least about 65%, at least about 70%, at least about 75%, at least about 80%, at least about 85%, at least about 90%, or at least about 95% of its biological activity (e.g., binding to the target, or therapeutic potency) exhibited before storage, i.e., at the time the pharmaceutical formulation was prepared.

In some embodiments, the isolated anti-PDL1 antibody is a glycated monoclonal antibody. In some embodiments, the glycated monoclonal antibody in the formulation comprises a light chain comprising the amino acid sequence of SEQ ID NO:9, and a heavy comprising the amino acid sequence of SEQ ID NO:10. In some embodiments, the glycated monoclonal antibody in the formulation comprises a heavy chain comprising the amino acid sequence of SEQ ID NO:10, wherein one or more of lysine is glycated. In some embodiments, the glycated monoclonal antibody in the formulation comprises a heavy chain comprising the amino acid sequence of SEQ ID NO:10, wherein K65 is glycated.

In some embodiments, the isolated anti-PDL1 antibody is aglycosylated.

In any of the embodiments herein, the isolated anti-PDL1 antibody can bind to a human PD-L1, for example a human PD-L1 as shown in UniProtKB/Swiss-Prot Accession No. Q9NZQ7.1, or a variant thereof.

In a still further embodiment, provided is an isolated nucleic acid encoding any of the antibodies described herein. In some embodiments, the nucleic acid further comprises a vector suitable for expression of the nucleic acid encoding any of the previously described anti-PDL1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PDL1 antibodies or antigen-binding fragment in a form suitable for expression, under conditions suitable to produce such antibody or fragment, and recovering the antibody or fragment.

B. Antibody Preparation

The antibody in the formulation is prepared using techniques available in the art for generating antibodies, exemplary methods of which are described in more detail in the following sections.

The antibody is directed against an antigen of interest (i.e., PD-L1, such as human PD-L1). Preferably, the antigen is a biologically important polypeptide and administration of the antibody to a mammal suffering from a disorder can result in a therapeutic benefit in that mammal.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., Nature, 256:495 (1975), and further described, e.g., in Hongo et al., Hybridoma, 14 (3): 253-260 (1995), Harlow et al., Antibodies: A laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), and Ni, Xiandai Mianyixue, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, Histology and Histopathology, 20(3):927-937 (2005) and Vollmers and Brandlein, Methods and Findings in Experimental and Clinical Pharmacology, 27(3):185-91 (2005).

For various other hybridoma techniques, see. e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, Monoclonal Antibodies: Principles and Practice, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VII and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.,* 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the loxP system described in Waterhouse et al., *Nucl. Acids Res.,* 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA,* 88: 7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.,* 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique* 1: 11-15 (1989)) in the method of Hawkins et al., *J. Mol. Biol.,* 226: 889-896 (1992) or in the method of Gram et al., *Proc. Natl. Acad. Sci USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones, WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,*

10: 779-783 (1992). This technique allows the production of antibodies and antibody fragments with affinities of about $10^{-9}$ M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by antigen competition, e.g. in a procedure similar to the antigen competition method of Clackson et al., *Nature*, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs.* 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*. 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature.* 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See. e.g., Jakobovits et al, *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach. F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al. *J. Immunol,* 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham. Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media. e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics. 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et. al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example. Enterobacteriaceae such as *Escherichia*, e.g., *E. coli. Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266.710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27.325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16.045), *K. wickeramii* (ATCC 24.178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see. e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available. e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, petunia, tomato, duckweed (Leninaceae), alfalfa (*M. truncatula*), and tobacco can also be utilized as hosts. See. e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo. ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S.

Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H^3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

C. Selecting Biologically Active Antibodies

Antibodies produced as described above may be subjected to one or more "biological activity" assays to select an antibody with beneficial properties from a therapeutic perspective or selecting formulations and conditions that retain biological activity of the antibody. The antibody may be tested for its ability to bind the antigen against which it was raised. For example, for an anti-PDL1 antibody, the antigen binding properties of the antibody can be evaluated in an assay that detects the ability to bind to PDL1. In some embodiments, the binding of the antibody may be determined by saturation binding, ELISA; and/or competition assays (e.g. RIA's), for example. Also, the antibody may be subjected to other biological activity assays, e.g., in order to evaluate its effectiveness as a therapeutic. Such assays are known in the art and depend on the target antigen and intended use for the antibody. For example, the biological effects of PD-L1 blockade by the antibody can be assessed in CD8+ T cells, a lymphocytic choriomeningitis virus (LCMV) mouse model and/or a syngeneic tumor model e.g., as described in U.S. Pat. No. 8,217,149.

To screen for antibodies which bind to a particular epitope on the antigen of interest (e.g., those which block binding of the anti-PDL1 antibody of the example to PD-L1), a routine cross-blocking assay such as that described in *Antibodies, A Laboratory Manual*, Cold Spring Harbor Laboratory, Ed Harlow and David Lane (1988), can be performed. Alternatively, epitope mapping. e.g. as described in Champe et al., *J. Biol. Chem.* 270:1388-1394 (1995), can be performed to determine whether the antibody binds an epitope of interest.

D. Preparation of the Formulations

After preparation of the antibody of interest (e.g., techniques for producing antibodies which can be formulated as disclosed herein will be elaborated below and are known in the art), the pharmaceutical formulation comprising it is prepared. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an F(ab')$_2$, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 25 mg/mL to about 150 mg/mL, or from about 30 mg/mL to about 140 mg/mL, or from about 35 mg/mL to about 130 mg/mL, or from about 40 mg/mL to about 120 mg/ml, or from about 50 mg/mL to about 130 mg/mL, or from about 50 mg/mL to about 125 mg/mL, or from about 50 mg/mL to about 120 mg/mL, or from about 50 mg/mL to about 110 mg/mL, or from about 50 mg/mL to about 100 mg/mL, or from about 50 mg/mL to about 90 mg/mL, or from about 50 mg/mL to about 80 mg/mL, or from about 54 mg/mL to about 66 mg/mL is an exemplary antibody concentration in the formulation.

An aqueous formulation is prepared comprising the antibody in a pH-buffered solution. The buffer of this invention has a pH in the range from about 5.0 to about 7.0. In certain embodiments the pH is in the range from about 5.0 to about 6.5, the pH is in the range from about 5.0 to about 6.4, in the range from about 5.0 to about 6.3, the pH is in the range from about 5.0 to about 6.2, the pH is in the range from about 5.0 to about 6.1, the pH is in the range from about 5.5 to about 6.1, the pH is in the range from about 5.0 to about 6.0, the pH is in the range from about 5.0 to about 5.9, the pH is in the range from about 5.0 to about 5.8, the pH is in the range from about 5.1 to about 6.0, the pH is in the range from about 5.2 to about 6.0, the pH is in the range from about 5.3 to about 6.0, the pH is in the range from about 5.4 to about 6.0, the pH is in the range from about 5.5 to about 6.0, the pH is in the range from about 5.6 to about 6.0, the pH is in the range from about 5.7 to about 6.0, or the pH is in the range from about 5.8 to about 6.0. In certain embodiments of the invention, the formulation has a pH of 6.0 or about 6.0. In certain embodiments of the invention, the formulation has a pH of 5.9 or about 5.9. In certain embodiments of the invention, the formulation has a pH of 5.8 or about 5.8. In certain embodiments of the invention, the formulation has a pH of 5.7 or about 5.7. In certain embodiments of the invention, the formulation has a pH of 5.6 or about 5.6. In certain embodiments of the invention, the formulation has a pH of 5.5 or about 5.5. In certain embodiments of the invention, the formulation has a pH of 5.4 or about 5.4. In certain embodiments of the invention, the formulation has a pH of 5.3 or about 5.3. In certain embodiments of the invention, the formulation has a pH of 5.2 or about 5.2. Examples of buffers that will control the pH within this range include histidine (such as L-histidine) or sodium acetate. In certain embodiments, the buffer contains histidine acetate or sodium acetate in the concentration of about 15 mM to about 25 mM. In certain embodiments of the invention, the buffer contains histidine acetate or sodium acetate in the concentration of about 15 mM to about 25 mM, about 16 mM to about 25 mM, about 17 mM to about 25 mM, about 18 mM to about 25 mM, about 19 mM to about 25 mM, about 20 mM to about 25 mM, about 21 mM to about 25 mM, about 22 mM to about 25 mM, about 15 mM, about 16 mM, about 17 mM, about 18 mM, about 19 mM, about 20 mM, about 21 mM, about 22 mM, about 23 mM, about 24 mM, or about 25 mM. In one embodiment, the buffer is histidine acetate or sodium acetate in an amount of about 20 mM, pH 5.0. In one embodiment, the buffer is histidine acetate or sodium acetate in an amount of about 20 mM, pH 5.1. In one embodiment, the buffer is histidine acetate or sodium acetate in an amount of about 20 mM, pH 5.2. In one embodiment, the buffer is histidine acetate or sodium acetate in an amount of about 20 mM, pH 5.3. In one embodiment, the buffer is histidine acetate or sodium acetate in an amount of about 20 mM, pH 5.4. In one embodiment, the buffer is histidine acetate or sodium acetate in an amount of about 20 mM, pH 5.5. In one embodiment, the buffer is histidine acetate or sodium acetate in an amount of about 20 mM, pH 5.6. In one embodiment, the buffer is histidine acetate or sodium acetate in an amount of about 20 mM, pH 5.7. In one embodiment, the buffer is histidine acetate or sodium acetate in an amount of about 20 mM, pH 5.8. In one embodiment, the buffer is histidine acetate or sodium acetate in an amount of about 20 mM, pH 5.9. In one embodiment, the buffer is histidine acetate or sodium acetate in an amount of about 20 mM, pH 6.0. In one embodiment, the buffer is histidine acetate or sodium acetate in an amount of about 20 mM, pH 6.1. In one embodiment, the buffer is histidine acetate or sodium acetate in an amount of about 20 mM, pH 6.2. In one embodiment, the buffer is histidine acetate or sodium acetate in an amount of about 20 mM, pH 6.3. In one embodiment, the buffer is histidine acetate or sodium acetate in an amount of about 25 mM, pH 5.2. In one embodiment, the buffer is histidine acetate or sodium acetate in an amount of about 25 mM, pH 5.3. In one embodiment, the buffer is histidine acetate or sodium acetate in an amount of about 25 mM, pH 5.4. In one embodiment, the buffer is histidine acetate or sodium acetate in an amount of about 25 mM, pH 5.5. In one embodiment, the buffer is histidine acetate or sodium acetate in an amount of about 25 mM, pH 5.6. In one embodiment, the buffer is histidine acetate or sodium acetate in an amount of about 25 mM, pH 5.7. In one embodiment, the buffer is histidine acetate or sodium acetate in an amount of about 25 mM, pH 5.8. In one embodiment, the buffer is histidine acetate or sodium acetate in an amount of about 25 mM, pH 5.9. In one embodiment, the buffer is histidine acetate or sodium acetate in an amount of about 25 mM, pH 6.0. In one embodiment, the buffer is histidine acetate or sodium acetate in an amount of about 25 mM, pH 6.1. In one embodiment, the buffer is histidine acetate or sodium acetate in an amount of about 25 mM, pH 6.2. In one embodiment, the buffer is histidine acetate or sodium acetate in an amount of about 25 mM, pH 6.3.

The formulation further comprises sucrose in an amount of about 60 mM to about 240 mM. In some embodiments, sucrose in the formulation is about 60 mM to about 230 mM, about 60 mM to about 220 mM, about 60 mM to about 210 mM, about 60 mM to about 200 mM, about 60 mM to about 190 mM, about 60 mM to about 180 mM, about 60 mM to about 170 mM, about 60 mM to about 160 mM, about 60 mM to about 150 mM, about 60 mM to about 140 mM, about 80 mM to about 240 mM, about 90 mM to about 240 mM, about 100 mM to about 240 mM, about 110 mM to about 240 mM, about 120 mM to about 240 mM, about 130 mM to about 240 mM, about 140 mM to about 240 mM, about 150 mM to about 240 mM, about 160 mM to about 240 mM, about 170 mM to about 240 mM, about 180 mM to about 240 mM, about 190 mM to about 240 mM, about 200 mM to about 240 mM, about 80 mM to about 160 mM, about 100 mM to about 140 mM, or about 110 mM to about 130 mM. In some embodiments, sucrose in the formulation is about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, or about 240 mM.

In some embodiments, the antibody concentration in the formulation is about 40 mg/ml to about 125 mg/ml. In some embodiments, the antibody concentration in the formulation is about 40 mg/ml to about 120 mg/ml, about 40 mg/ml to about 110 mg/ml, about 40 mg/ml to about 100 mg/ml, about 40 mg/ml to about 90 mg/ml, about 40 mg/ml to about 80 mg/ml, about 40 mg/ml to about 70 mg/ml, about 50 mg/ml to about 120 mg/ml, about 60 mg/ml to about 120 mg/ml, about 70 mg/ml to about 120 mg/ml, about 80 mg/ml to about 120 mg/ml, about 90 mg/ml to about 120 mg/ml, or about 100 mg/ml to about 120 mg/ml. In some embodiments, the antibody concentration in the formulation is about 60 mg/ml. In some embodiments, the antibody concentration in the formulation is about 65 mg/ml. In some embodiments, the antibody concentration in the formulation is about 70 mg/ml. In some embodiments, the antibody concentration in the formulation is about 75 mg/ml. In some embodiments, the antibody concentration in the formulation is about 80 mg/ml. In some embodiments, the antibody concentration in the formulation is about 85 mg/ml. In some embodiments, the antibody concentration in the formulation is about 90 mg/ml. In some embodiments, the antibody concentration in the formulation is about 95 mg/ml. In some embodiments, the antibody concentration in the formulation is about 100 mg/ml. In some embodiments, the antibody concentration in the formulation is about 110 mg/ml. In some embodiments, the antibody concentration in the formulation is about 125 mg/ml.

In some embodiments, a surfactant is added to the antibody formulation. Exemplary surfactants include nonionic surfactants such as polysorbates (e.g. polysorbates 20, 80 etc) or poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5% (w/v). In some embodiments, the surfactant (e.g., polysorbate 20) is from about 0.005% to about 0.2%, from about 0.005% to about 0.1%, from about 0.005% to about 0.09%, from about 0.005% to about 0.08%, from about 0.005% to about 0.07%, from about 0.005% to about 0.06%, from about 0.005% to about 0.05%, from about 0.005% to about 0.04%, from about 0.008% to about 0.06%, from about 0.01% to about 0.06%, from about 0.02% to about 0.06%, from about 0.01% to about 0.05%, or from about 0.02% to about 0.04%. In certain embodiments, the surfactant (e.g., polysorbate 20) is present in the formulation in an amount of 0.005% or about 0.005%. In certain embodiments, the surfactant (e.g., polysorbate 20) is present in the formulation in an amount of 0.006% or about 0.006%. In certain embodiments, the surfactant (e.g., polysorbate 20) is present in the formulation in an amount of 0.007% or about 0.007%. In certain embodiments, the surfactant (e.g., polysorbate 20) is present in the formulation in an amount of 0.008% or about 0.008%. In certain embodiments, the surfactant (e.g., polysorbate 20) is present in the formulation in an amount of 0.009% or about 0.009%. In certain embodiments, the surfactant (e.g., polysorbate 20) is present in the formulation in an amount of 0.01% or about 0.01%. In certain embodiments, the surfactant (e.g., polysorbate 20) is present in the formulation in an amount of 0.02% or about 0.02%. In certain embodiments, the surfactant (e.g., polysorbate 20) is present in the formulation in an amount of 0.03% or about 0.03%. In certain embodiments, the surfactant (e.g., polysorbate 20) is present in the formulation in an amount of 0.04% or about 0.04%. In certain embodiments, the surfactant (e.g., polysorbate 20) is present in the formulation in an amount of 0.05% or about 0.05%. In certain embodiments, the surfactant (e.g., polysorbate 20) is present in the formulation in an amount of 0.06% or about 0.06%. In certain embodiments, the surfactant (e.g., polysorbate 20) is present in the formulation in an amount of 0.07% or about 0.07%. In certain embodiments, the surfactant (e.g., polysorbate 20) is present in the formulation in an amount of 0.08% or about 0.08%. In certain embodiments, the surfactant (e.g., polysorbate 20) is present in the formulation in an amount of 0.1% or about 0.1%. In certain embodiments, the surfactant (e.g., polysorbate 20) is present in the formulation in an amount of 0.2% or about 0.2%. In certain embodiments, the surfactant (e.g., polysorbate 20) is present in the formulation in an amount of 0.3% or about 0.3%. In certain embodiments, the surfactant (e.g., polysorbate 20) is present in the formulation in an amount of 0.4% or about 0.4%. In certain embodiments, the surfactant (e.g., polysorbate 20) is present in the formulation in an amount of 0.5% or about 0.5%.

In one embodiment, the formulation contains the above-identified agents (e.g., antibody, buffer, sucrose, and/or surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions. Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein may also contain more than one protein as necessary for the particular indication being treated, preferably those with complementary activities that do not adversely affect the other protein. For example, where the antibody is anti-PDL1, it may be combined with another agent (e.g., a chemotherapeutic agent, and anti-neoplastic agent).

In some embodiments, the physical stability, chemical stability, or biological activity of the antibody in the formulation is evaluated or measured. Any methods known in the art and described in the Examples herein may be used to evaluate the stability and biological activity of the antibody in the formulation. For example, stability of the antibody in the formulation can be measured by, but not limited to, size exclusion chromatography (SEC or SE-HPLC), imaged capillary isoelectric focusing (ICIEF), peptide mapping, small-volume light obscuration (HIAC) assay, and capillary electrophoresis (CE) techniques such as CE-sodium dodecyl sulfate (CE-SDS) and CE-glycan analysis. In some embodiments, the antibody in the formulation is stable at −20° C. for at least about 6 months, at least about 8 months, at least about 10 months, at least about 12 months, at least about 14 months, at least about 16 months, at least about 18 months, at least about 20 months, at least about 21 months, at least about 22 months, at least about 23 months, at least about 24 months, at least about 3 years, or at least about 4 years. In some embodiments, the antibody in the formulation is stable at 2° C. to 8° C. (e.g., 5° C.) for at least about 6 months, at least about 8 months, at least about 10 months, at least about 12 months, at least about 14 months, at least about 16 months, at least about 18 months, at least about 20 months, at least about 21 months, at least about 22 months, at least about 23 months, or at least about 24 months. In some embodiments, the stability of the antibody (i.e., an antibody monomer) is measured by size exclusion chromatography in the formulation after storage. In some embodiments, the stability of the antibody is (i.e., an antibody monomer) measured by imaged capillary isoelectric focusing in the formulation after storage. In some embodiments, the percent of antibody monomer in the formulation as compared to total protein (e.g., including antibody and aggregates) is greater than about 60%, about 65%, about 70%, about 75%, about 80%, about 85%, about 86%, about 87%, about 88%, about 89%, about 90%, about 91%, about 92%, about 93%, about 94% or about 95% after storage at −20° C. for at least about 6 months, at least about 12 months, at least about 18 months, or at least about 24 months. In some embodiments, the percent of antibody monomer in the formulation as compared to (e.g., including antibody and aggregates) is greater than about 60%, about 65%, about 70%, about 75%, about 80%, about 85%, about 86%, about 87%, about 88%, about 89%, about 90%, about 91%, about 92%, about 93%, about 94% or about 95% after storage at 2° C. to 8° C. (e.g., 5° C.) for at least about 6 months, at least about 12 months, at least about 18 months, or at least about 24 months. In some embodiments, the percent of antibody monomer in the formulation as compared to (e.g., including antibody and aggregates) is greater than about 60%, about 65%, about 70%, about 75%, about 80%, about 85%, about 86%, about 87%, about 88%, about 89%, about 90%, about 91%, about 92%, about 93%, about 94% or about 95% after agitation at room temperature (e.g., about 15° C. to 25° C.) for at least about 2 hours, at least about 4 hours, at least about 6 hours, at least about 8 hours, at least about 10 hours, at least about 12 hours, at least about 14 hours, at least about 16 hours, at least about 18 hours, at least about 20 hours, or at least about 24 hours. In some embodiments, the percent of total aggregates (e.g., high molecular weight species and low molecular weight species) in the formulation is less than any of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% after storage at −20° C. for at least about 6 months, at least about 12 months, at least about 18 months, or at least about 24 months. In some embodiments, the percent of total aggregates (e.g., high molecular weight species and low molecular weight species) in the formulation is less than any of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% after storage at 2° C. to 8° C. (e.g., 5° C.) for at least about 6 months, at least about 12 months, at least about 18 months, or at least about 24 months. In some embodiments, the percent of total aggregates (e.g., high molecular weight species and low molecular weight species) in the formulation is less than any of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% after agitation at room temperature (e.g., about 15° C. to 25° C.) for at least about 2 hours, at least about 4 hours, at least about 6 hours, at least about 8 hours, at least about 10 hours, at least about 12 hours, at least about 14 hours, at least about 16 hours, at least about 18 hours, at least about 20 hours, or at least about 24 hours. In any of the embodiments herein, the stable formulation can be stored in a glass vial, a metal alloy container, or an intravenous (IV) bag. In some embodiments, the metal alloy is 316L stainless steel or hastelloy.

The formulations to be used for in vivo administration should be sterile. This is readily accomplished by filtration through sterile filtration membranes, prior to, or following, preparation of the formulation.

III. Methods of Treatment and Administration of Antibody Formulations

The formulation is administered to a mammal in need of treatment with the antibody, preferably a human, in accord with known methods, such as intravenous administration (e.g., as a bolus or by continuous infusion over a period of time), by intramuscular, intraperitoneal, intracerobrospinal, subcutaneous, intra-articular, intrasynovial, intrathecal, oral, topical, or inhalation routes. In one embodiment, the formulation is administered to the mammal by intravenous administration. For such purposes, the formulation may be injected using a syringe or via an IV line, for example. In one embodiment, the formulation is administered to the mammal by subcutaneous administration.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered to human will be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PDL1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

The formulations containing anti-PDL1 antibody described herein can be used in a variety of in vitro and in vivo diagnostic and therapeutic applications. For example, the formulation containing the antibody may be administered to a subject or an individual for treating a disease or disorder (e.g., disease or disorder mediated by the PD-1 and PD-L1 interaction).

In some embodiments, the disease or disorder is cancer. In some embodiments, the cancer is locally advanced or metastatic. In some embodiments, the cancer is selected from the group consisting of a solid tumor, a hematologic cancer, bladder cancer, brain cancer, breast cancer, colon cancer, colorectal cancer, gastric cancer, glioma, head cancer, leukemia, liver cancer, lung cancer (e.g., non-small cell lung cancer), lymphoma, myeloma, neck cancer, ovarian cancer, melanoma, pancreatic cancer, renal cancer, salivary cancer, stomach cancer, thymic epithelial cancer, thyroid cancer, and squamous cell carcinoma of the head and neck. In some embodiments, the subject or individual treated has PD-L1 positive cancer cells (e.g., detected by IHC).

In some embodiments, the disease or disorder is infection. In some embodiments, the infection is a persistent infection. In some embodiments, the infection is a viral infection, a bacterial infection, a fungal infection, a helminth infection, or a protozoan infection. In some embodiments, the viral infection is selected from the group consisting of cytomegalovirus Epstein-Barr virus, hepatitis B, hepatitis C virus, herpes virus, measles virus, influenza, human immunodeficiency virus, human T lymphotropic virus, lymphocytic choriomeningitis virus, respiratory syncytial virus, and/or rhinovirus. In some embodiments, the bacterial infection is selected from the group consisting of *Helicobacter* spp., *Mycobacterium* spp., *Porphyromonas* spp., *Chlamydia* spp., *Salmonella* spp., *Listeria* spp., *Streptococcus* spp., *Haemophilus* spp., *Neisseria* spp., *Klebsiella* sp., *Borrelia* spp., *Bacterioides* spp., and *Treponema* spp. In some embodiments, the protozoan infection is selected from the group consisting of *Leishmania* spp., *Plasmodium falciparum*, *Schistosoma* spp., *Toxoplasma* spp., *Trypanosoma* spp., and *Taenia* spp. In some embodiments, the fungal infection is selected from the group consisting of blastonmycosis, coccidioiodmycosis, histoplamsosis, candidiasis, cryptococcosis, aspergillossi, mucomycosis and pneumocystosis.

In some embodiments, the disease or disorder is an inflammatory disease. In some embodiments, the inflammatory disease is selected from the group consisting of acute disseminated encephalomyelitis. Addison's disease, Alzheimer's disease, ankylosing spondylitis, antiphospholipid antibody syndrome, atherosclerosis, autoimmune hemolytic anemia, autoimmune hepatitis, arthritis, Behcet's disease, Berger's disease, Bullous pemphigoid, Celiac disease, Chagas' disease, cholangitis, Crohn's disease, Dermatomyositis, Diabetes mellitus type 1, glomerulonephritis, Goodpasture's syndrome, graft-versus-host disease, Graves' disease, Guillain-Barré syndrome, Hashimoto's disease, hives, hyper IgE syndrome, idiopathic thrombocytopenic purpura, lupus erythematosus, lupus nephritis, multiple sclerosis, myasthenia gravis, organ transplant rejection, Parkinson's disease, pemphigus, pernicious anaemia, polymyositis, primary biliary cirrhosis, psoriasis, Raynaud's syndrome, rheumatoid arthritis, scleroderma. Sjögren's syndrome, temporal arteritis, thyroiditis, ulcerative colitis, uveitis, vasculitis, and Wegener's granulomatosis.

In some embodiments, the formulation containing the antibody may be administered in conjunction with another therapeutic agent to a subject or an individual for treating a disease or disorder. For example, for treating cancer, the anti-PDL1 antibody formulation described herein may administered in conjunction with another anti-cancer treatment (e.g., a chemotherapy or a different antibody treatment).

IV. Articles of Manufacture or Kits

In another embodiment of the invention, an article of manufacture or a kit is provided comprising a container which holds the aqueous pharmaceutical formulation of the invention and optionally provides instructions for its use. Suitable containers include, for example, bottles, vials, bags and syringes. The container may be formed from a variety of materials such as glass, plastic (such as polyvinyl chloride or polyolefin), or metal alloy (such as stainless steel or hastelloy). An exemplary container is a 300 cc metal alloy container (e.g., for storing at −20° C.). Another exemplary container may be 10-50 cc glass vial (e.g., for storing at 2-8° C.). For example, the container may be 10 cc, 15 cc, 20 cc, or 50 cc glass vials. The container holds the formulation and the label on, or associated with, the container may indicate directions for use. The article of manufacture may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Formulation Development of an Anti-PDL1 Antibody

Anti-PDL1 antibody (α-PDL1) is a CHO-derived aglycosylated IgG1 antibody intended to restore T cell function through inhibition of PDL1/PD1 interactions. Challenges at the outset of development included potential Trp oxidation and glycation in or near CDR regions and some methionine oxidation. Pre-robustness studies indicated a higher pH than previously targeted (pH 5.5) was optimal. The target dosing was a fixed dose but a weight based dose was also contemplated. Analytical studies were conducted to analyze stability of various formulations and a formulation (60 mg/mL α-PDL1, 20 mM His AcO pH 5.8, 120 mM sucrose, 0.04% PS20) was selected. Initial formulation studies support up to three years of stability in Drug Substance (DS) and Drug Product (DS).

Methods and Materials
Production of α-PDL1 Formulations

α-PDL1 material that had undergone ultrafiltration/diafiltration was subjected to formulation development studies. The material was dialyzed into various formulation buffers using 10000 Dalton dialysis cassettes. After dialysis, protein concentrations were adjusted to reach target concentrations and 10% PS20 stock solution was spiked in to achieve targeted PS20 concentrations. The formulated material was filled aseptically into 2-cc Forma Vitrum glass vials with 1 mL fill volume and sealed with a 13 mm Daikyo 777-1 stopper. Samples were stored upright at either 5° C., 25° C., or 40° C.

Color, Appearance, and Clarity (CAC)

Sample color, appearance, and clarity were determined by visual inspection under a white fluorescence light with black and white background at room temperature as described in the European Pharmacopoeia (EP) methods (Council of Europe. *European Pharmacopoeia*, 2008, 7$^{th}$ Ed., EP 2.2.2 and EP 2.2.1). A 3 cc glass vial was filled with 1 mL of each sample tested. A negative control (purified water) with the corresponding sample volume was used for comparison.

Protein Concentration Measurements

The protein concentration was determined by measurement of the UV-absorbance on an Agilent 8453 spectrophotometer (Santa Clara, Calif.) via volumetric sample dilution to approximately 0.5 mg/mL with 0.9% saline. The samples were blanked against 0.9% saline and the absorbance was measured at the $A_{max}$ of approximately 280 nm and also at 320 nm. The difference between $A_{max}$ and $A_{320}$ was calculated to obtain the corrected $A_{max}$ used to determine the final protein concentration with an absorptivity of 1.5 mL cm$^{-1}$ mg$^{-1}$.

Turbidity Measurements

The average optical density at 350 nm of the samples was measured in a quartz cuvette with a 1-cm path length on an Agilent 8453 spectrophotometer. Purified water was used as a blank.

Light Obscuration Method for Subvisible Particles (HIAC Assay)

Particulate counts of samples were performed using light obscuration measured by the HIAC-Royco model 9703 (HACH, Loveland, Colo.). Average cumulative numbers of particles per milliliter ≥2 µm, ≥5 µm, ≥10 µm and ≥25 µm were tabulated for each sample using PharmSpec v2.0. Four readings, consuming a total of 1.6 mL of each sample, were performed per test, with the first reading discarded, and the remaining 3 readings averaged.

Size Exclusion Chromatography (SEC or SE-HPLC)

Size variant distribution was determined by size exclusion chromatography (SEC) using a TosoHaas Bioscience column G3000 SWXL (South San Francisco, Calif.) at 30° C. on an Agilent 1200 HPLC (Santa Clara, Calif., USA). All samples were injected undiluted at 50 µg onto the column and eluted over 60 minutes with UV absorption at 280 nm. Two different SEC methods were used for sample testing. Method 1 used 0.20 M potassium phosphate, 0.25 M potassium chloride, pH 6.2, while method 2 used 0.20 M potassium phosphate, 0.25 M potassium chloride, pH 6.2 with 10% (v/v) isopropanol as the mobile phase. Results are reported as relative percent peak area of the total area under the curve.

Imaged Capillary Isoelectric Focusing (ICIEF)

The distribution of charge variants was assessed by iCIEF using an iCE280 analyzer (ProteinSimple) with a fluorocarbon coated capillary cartridge (100 µm×5 cm). The ampholyte solution consisted of a mixture of 0.35% methyl cellulose (MC), 0.75% Pharmalyte 3-10 carrier ampholytes, 4.2% Pharmalyte 8-10.5 carrier ampholytes, and 0.2% pI marker 7.40 and 0.15% pI marker 9.77 in purified water. The anolyte was 80 mM phosphoric acid, and the catholyte was 100 mM sodium hydroxide, both in 0.10% methylcellulose. Samples were diluted in purified water and CpB was added to each diluted sample at an enzyme to substrate ratio of 1:100 followed by incubation at 37° C. for 20 minutes. The CpB treated samples were mixed with the ampholyte solution and then focused by introducing a potential of 1500 V for one minute, followed by a potential of 3000 V for 10 minutes. An image of the focused α-PDL1 charge variants was obtained by passing 280 nm ultraviolet light through the capillary and into the lens of a charge coupled device digital camera. This image was then analyzed to determine the distribution of the various charge variants.

Peptide Mapping

A peptide mapping technique was used to monitor tryptophan (W) and methionine (M) oxidation. To generate α-PDL1 peptide maps, the protein was digested with trypsin after exposing the protein to dithiothreitol (DTT) and iodoacetic acid (IAA), in a process that reduces the disulfide bonds and alters the resultant free thiols to produce carboxymethyl derivatives. The resulting peptides were separated by reversed-phase high-performance liquid chromatography (RP-HPLC) and monitored at 214 nm. Masses of the tryptic peptides were determined by LC-MS analysis of the separated digest mixture using a ThermoFisher Scientific LTQ-Orbitrap mass spectrometer.

Results

Selection of Buffer System

During formulation development, two buffer systems were evaluated. One was 20 mM histidine acetate with 240 mM sucrose at pH 5.5, the other one was 200 mM arginine succinate at pH 5.5. The accelerated stability study revealed that α-PDL1 has better stability in histidine acetate buffer compared to arginine succinate buffer (Table 1). Therefore histidine acetate was chosen for further development of formulations.

TABLE 1

Zero-Order Degradation Rates of α-PDL1 for ICIEF and SE-HPLC Main Peak in Histidine Acetate and Arginine Succinate buffers at 30° C.

| Buffers | Rate of % Main Peak Decrease per Month at 30 C. | |
| --- | --- | --- |
| | ICIEF | SE-HPLC |
| Histidine Acetate* | 5.7 | 1.0 |
| Arginine Succinate** | 17.6 | 1.5 |

Note:
All formulations were stored for up to 1 month at 30° C. Analysis was performed using ICIEF and SE-HPLC;
*150 mg/mL α-PDL1 in 20 mM L-histidine acetate, 240 mM sucrose, and 0.02% (w/v) polysorbate 20 at pH 5.5;
**150 mg/mL α-PDL1 in 200 mM arginine succinate, 0.02% (w/v) polysorbate 20 at pH 5.5.

Selection of Stabilizer

Sucrose (120 mM) was selected as the stabilizer for the α-PDL1 liquid formulation based on its ability to protect the protein from freeze/thaw induced aggregation as well as function as a cryoprotectant during long-term frozen storage of the Drug Substance (DS) and subsequent Drug Product (DP) storage at 2° C.-8° C.

During formulation development, α-PDL1 at 50 mg/mL in 20 mM L-histidine acetate, pH 5.5, 0.02% (w/v) polysorbate 20, and various concentrations of sucrose ranging from 0 mM to 120 mM was subjected to five freeze/thaw cycles. Product quality measured by SE-HPLC indicated that 60 mM sucrose was sufficient to prevent a freeze/thaw induced increase in α-PDL1 HMWS (Table 2). Also, 120 mM sucrose was shown to maintain stability of the Drug Substance when stored frozen at −20° C. for at least 6 months (Table 3). Therefore, based upon results from the freeze/thaw studies as well as the long-term stability of Drug Substance stored at −20° C., sucrose at a concentration of 120 mM was chosen as the cryoprotectant for the α-PDL1 liquid formulation.

TABLE 2

Effect of Sucrose Concentration on Stability of α-PDL1 SE-HPLC Percent High-Molecular-Weight Species during Freezing and Thawing

| Sucrose Conc. (mM) | F/T cycles | SE-HPLC % HMWS | SE-HPLC % Monomer | CAC | pH |
|---|---|---|---|---|---|
| T0 | NA | 1.2 | 98.8 | SY, CL, PFVP | 5.6 |
| 0 mM | 5 | 1.4 | 98.6 | SY, CL, PFVP | 5.7 |
| 60 mM | 5 | 1.2 | 98.8 | SY, CL, PFVP | 5.7 |
| 120 mM | 5 | 1.2 | 98.8 | SY, CL, PFVP | 5.6 |

Note:
All formulations contain 50 mg/mL α-PDL1, 20 mM L-histidine acetate, 0.02% (w/v) polysorbate 20, pH 5.5. Analysis was performed using SE-HPLC; F/T = freeze/thaw; HMWS = high-molecular-weight species: SY = slightly yellow; CL = clear: PFVP = practically free of visible particles.

TABLE 3

Long Term Stability Data for α-PDL1 Drug Substance Development Batch

| Temp (° C.) | Time (days/ months) | Q12005 CAC | Q12003 pH | Q12398 Strength (mg/mL) | Q12631 ICIEF Acidic Region (area %) | Q12631 ICIEF Main Peak (area %) | Q12631 ICIEF Basic Region (area %) | Q12589 SEC Sum of HMW Forms (area %) |
|---|---|---|---|---|---|---|---|---|
| NA | T = 0/0 | SY, CL, PFVP | 5.9 | 60.1 | 17.3 | 79.7 | 3.0 | 0.7 |
| -20° C. | 30/1 | SY, CL, PFVP | 5.9 | 62.9 | 16.9 | 80.2 | 2.9 | 0.6 |
| -20° C. | 61/2 | SY, CL, PFVP | 5.9 | 61.4 | 16.5 | 80.8 | 2.7 | 0.6 |
| -20° C. | 91/3 | SY, CL, PFVP | 5.9 | 62.5 | 18.1 | 79.0 | 3.0 | 0.6 |
| -20° C. | 183/6 | SY, CL, PFVP | 5.9 | 61.1 | 17.9 | 79.0 | 3.1 | 0.6 |
| 5° C. | 30/1 | SY, CL, PFVP | 5.9 | 61.1 | 18.1 | 79.0 | 2.9 | 0.7 |
| 5° C. | 61/2 | SY, CL, PFVP | 5.9 | 62.3 | 17.4 | 79.8 | 2.8 | 0.8 |
| 5° C. | 91/3 | SY, CL, PFVP | 5.9 | 63.9 | 17.4 | 80.1 | 2.5 | 0.9 |
| 5° C. | 183/6 | SY, CL, PFVP | 5.9 | 59.5 | 19.7 | 77.4 | 3.0 | 1.1 |

| Temp (° C.) | Q12589 SEC Monomer Peak (area %) | Q12589 SEC LMW Forms (area %) | Q12695 CE-SDS-NGS (non-reduced) Sum of Pre-Peaks (% CPA) | Q12695 CE-SDS-NGS (non-reduced) Main Peak (% CPA) | Q12695 CE-SDS-NGS (non-reduced) Sum of Post-Peaks (% CPA) | Q12708 Potency (% relative potency) |
|---|---|---|---|---|---|---|
| NA | 99.2 | 0.1 | 2.7 | 97.0 | 0.3 | 107 |
| -20° C. | 99.3 | 0.1 | 2.8 | 97.0 | 0.2 | 109 |
| -20° C. | 99.4 | 0.1 | 2.5 | 97.3 | 0.3 | NT |
| -20° C. | 99.3 | 0.1 | 2.8 | 97.1 | 0.2 | 96 |
| -20° C. | 99.4 | 0.1 | 3.1 | 96.6 | 0.3 | 100 |
| 5° C. | 99.2 | 0.1 | 2.6 | 97.0 | 0.4 | 101 |
| 5° C. | 99.2 | 0.1 | 2.9 | 96.7 | 0.4 | NT |
| 5° C. | 99.0 | 0.1 | 3.0 | 96.5 | 0.5 | 107 |
| 5° C. | 98.8 | 0.1 | 3.3 | 95.9 | 0.8 | 102 |

Note:
All formulations contain 60 mg/mL α-PDL1 in 20 mM L-histidine acetate, 120 mM sucrose, 0.04% PS20, pH 5.8.
25 cc 316 L stainless steel mini-cans were used for this study; NA = not applicable; CAC = color, appearance, and clarity; SY = slightly yellow, CL = clear, PFVP = practically free of visible particulates; HMW = high molecular weight; LMW = low molecular weight; ICIEF = imaged capillary isoelectric focusing; CE-SDS = capillary electrophoresis sodium dodecyl sulfate; NT = not tested; TBD = to be determined.

Pre-Formulation Robustness Studies: Selection of Protein Concentration, pH and Polysorbate 20 Concentration A fractional factorial design of experiments (DOE) design was used to further examine the effects of α-PDL1 formulation parameters on protein stability. A total of twelve different α-PDL1 formulations were tested (ten experiments and two center points). The three factors varied in the study were pH range of 5.0-6.0 with 0.5 unit intervals, protein concentration range of 40-120 mg/mL, and polysorbate 20 concentration range of 0.005%-0.06% (w/v) (Table 4). All formulations were buffered by 20 mM histidine acetate with 120 mM sucrose except the last two formulations as indicated in Table 4. The 25 mM histidine acetate formulation was evaluated since it was considered to be a worst case scenario in terms of oxidation risk. The 20 mM sodium acetate buffer was evaluated as a back-up buffer system and compared to histidine acetate buffer. The formulations were stored at 25° C. for 2 months and 40° C. for 1 month. The stability data from the above studies were statistically analyzed for interactions between the formulation parameters using JMP software (JMP, Version 9, SAS Institute Inc., Cary, N.C.).

TABLE 4

α-PDL1 Drug Substance and Drug Product
Formulations Evaluated in the DOE study

| Formulation | anti-PDL1 (mg/mL) | Solution pH | PS20 (% w/v) | His-Acetate (mM) | Sucrose (mM) |
|---|---|---|---|---|---|
| F1[a] | 50 | 5.5 | 0.04 | 20 | 120 |
| F2[a] | 100 | 5.5 | 0.04 | 20 | 120 |
| F3 | 40 | 6.0 | 0.06 | 20 | 120 |
| F4 | 120 | 5.0 | 0.06 | 20 | 120 |
| F5 | 120 | 6.0 | 0.005 | 20 | 120 |
| F6 | 40 | 5.0 | 0.06 | 20 | 120 |
| F7 | 120 | 5.0 | 0.005 | 20 | 120 |
| F8 | 40 | 6.0 | 0.005 | 20 | 120 |
| F9 | 40 | 5.0 | 0.005 | 20 | 120 |
| F10 | 120 | 6.0 | 0.06 | 20 | 120 |
| F11[b] | 50 | 5.5 | 0.06 | 25 | 120 |
| F12[c] | 50 | 5.5 | 0.04 | 20 (Na-Ace) | 120 |

Note:
[a]Center points;
[b]Worst case scenario: low protein concentration, high PS20 concentration, high histidine concentration;
[c]20 mM sodium acetase (Na-Ace) buffer was tested.

In comparison to pH 5.0 and 5.5, the formulation at pH 6.0 has slightly slower main peak loss rate, as determined by ICIEF at 40° C. and 25° C. (FIGS. 1A-B and FIGS. 2A-B, respectively). No significant impact of concentration on main peak loss was observed by ICIEF. Analysis of formulation F1 showed that an acidic variant increase contributed primarily to main peak loss in ICIEF while the contribution to peak loss by a basic charge variant was not significant. Under the same storage conditions, the formulation at pH 6.0 also had a slower monomer peak loss rate, as measured by SE-HPLC at 40° C. and 25° C. (FIGS. 3A-B and FIGS. 4A-B, respectively). Analysis of formulation F1 showed that both HMWS and LMWS formation contributed to monomer loss in SEC at elevated temperatures (i.e., 40° C. and 25° C.). Both the SEC and ICIEF pH rate profiles revealed that pH 5.5-6.0 is the optimal pH range for α-PDL1. To be within optimal protein stability above pH 5.5 and to allow for a ±0.3 pH unit range in the formulated Drug Substance and Drug Product, a target of pH 5.8 was chosen.

The above formulation studies also revealed that 120 mg/mL of α-PDL1 formulations at pH range of 5.0-6.0 had a slightly higher but non-significant monomer peak loss rate due to higher HMWS formation rate compared to 40 mg/mL formulations at the same pH, as determined by SE-HPLC (FIGS. 3A-B and FIGS. 4A-B). Based on these data and to support a formulation with improved product stability and to facilitate patient dosing. α-PDL1 at a concentration of 60 mg/mL was selected.

No impact on protein stability was observed with polysorbate 20 (PS20) concentrations ranging from 0.005%-0.06% (w/v) as indicated in the above statistical analysis (FIGS. 1-4).

It has been known that hydrogen peroxide impurity contained in polysorbate 20 raw material can cause tryptophan (W) and methionine (M) oxidation. L-histidine can also increase the above oxidation risk. The samples of selected worst case scenario formulations containing higher concentrations of polysorbate 20 and L-histidine were analyzed by peptide mapping. Results of the analysis showed that even the combination of higher histidine concentration (25 mM histidine acetate buffer) and higher amount of PS20 (0.06% PS20) didn't demonstrate significant oxidation risk (Table 5) and histidine buffer is suitable for use to formulate α-PDL1.

TABLE 5

Percentage of Trp and $M^{253}$ oxidation in Selected Formulations by Peptide Map

| | Selected Formulations | | | | % Oxidation | | | |
|---|---|---|---|---|---|---|---|---|
| | Conc. (mg/mL) | Buffer (mM) | PS20 (%) | Time points | W CDR HC2 | W CDR HC4 | W CDR HC10 | LC27 M253 |
| F1 | 50 | 20 mM His-Ace | 0.04 | T0 | 0.1 | 0.1 | 0.1 | 5.5 |
| F3 | 40 | 20 mM His-Ace | 0.06 | 25 C., 2 M | 0.2 | 0.2 | 0.2 | 6.4 |
| F10 | 120 | 20 mM His-Ace | 0.06 | 25 C., 2 M | 0.2 | 0.1 | 0.2 | 6.7 |
| F11 | 50 | 25 mM His-Ace | 0.06 | 25 C., 2 M | 0.2 | 0.2 | 0.2 | 6.6 |

Figure 5:
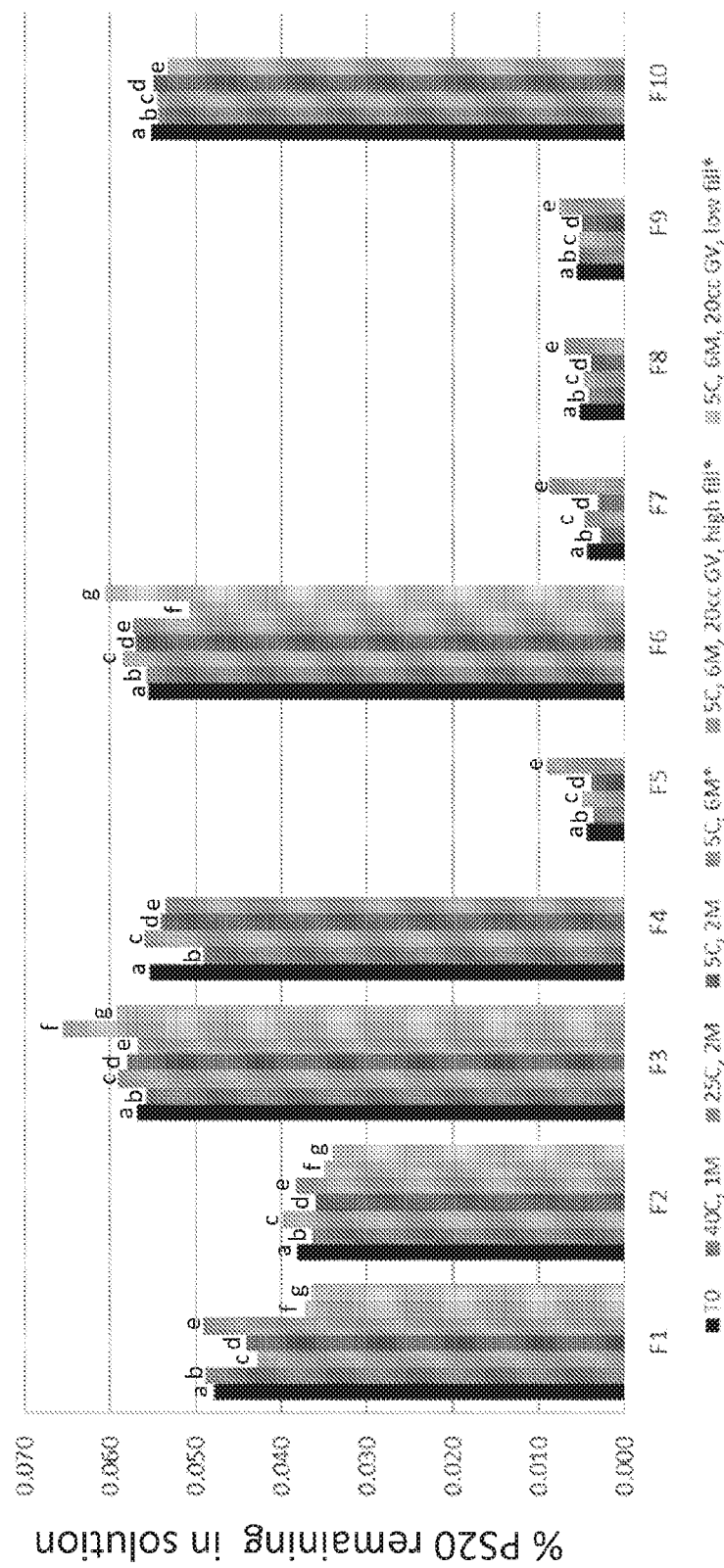
FIG. 5 is a graph showing lack of significant PS20 degradation of various α-PDL1 formulations stored at various temperatures and time. Graph of percent (%) PS20 remaining in the formulation as detected by evaporative light scattering detector (ELSD) in F1 through F10 formulations, a is time zero (T0); b is 40° C., 1M; c is 25° C., 2M; d is 5° C., 2M; e is 5° C., 6M; f is 5° C., 6M, 20 cc glass vial (GV), high fill; and g is 5° C., 6M, 20 cc glass vial (GV), low fill.

Note:
All formulations were stored for up to 1 month at 40° C.
Analysis was performed using Peptide map.
W = Tryptophan; M = Methionine To assess the possible degradation of PS20 in the formulation upon storage, Formulations F1 to F10 (Table 4) were stored at 40° C. for 1 month, 25° C. for 2 months, 5° C. for 2 months or 5° C. for 6 months. No PS20 degradation was observed in the evaluated formulations at the any of the elevated (i.e., 40° C. and 25° C.) and 5° C. storage temperature. Altering the fill volume of selected formulations (i.e., F1, F2, F3, and F6) to 7 ml (high fill) or 4 ml (low fill) and then storing at 5° C. for 6 months also did not have a significant impact on the PS20 degradation rate (FIG. 5).

The formation of sub-visible particles (SbVP) in the different formulations when stored at 5° C. for 6 months was assessed by the HIAC assay as a measure of stability (Table 6). No measureable change in SbVP was observed in the formulation tested.

TABLE 6

HIAC data for SbVP formation after 6 months storage at 5° C.

| | Time Point | Particle Size (Cumulative Counts/mL) | | | |
|---|---|---|---|---|---|
| Sample | (month) | 2 μM | 5 μM | 10 μM | 25 μM |
| F1 | 0 | 802 | 193 | 61 | 5 |
| | 6 | 1190 | 278 | 80 | 6 |
| F2 | 0 | 799 | 146 | 43 | 12 |
| | 6 | 370 | 112 | 29 | 2 |
| F3 | 0 | 485 | 133 | 34 | 4 |
| | 6 | 163 | 52 | 14 | 2 |

TABLE 6-continued

HIAC data for SbVP formation after 6 months storage at 5° C.

| Sample | Time Point (month) | Particle Size (Cumulative Counts/mL) | | | |
|---|---|---|---|---|---|
| | | 2 µM | 5 µM | 10 µM | 25 µM |
| F4 | 0 | 211 | 65 | 31 | 8 |
| | 6 | 181 | 48 | 8 | 1 |
| F5 | 0 | 872 | 359 | 195 | 79 |
| | 6 | 340 | 89 | 23 | 1 |
| F6 | 0 | 233 | 61 | 16 | 3 |
| | 6 | 116 | 34 | 16 | 3 |
| F7 | 0 | 134 | 29 | 13 | 4 |
| | 6 | 144 | 42 | 9 | 0 |
| F8 | 0 | 433 | 118 | 34 | 1 |
| | 6 | 564 | 98 | 23 | 2 |
| F9 | 0 | 498 | 114 | 17 | 1 |
| | 6 | 144 | 21 | 6 | 0 |
| F10 | 0 | 610 | 124 | 23 | 0 |
| | 6 | 248 | 75 | 28 | 3 |

Note:
Two 1 mL fill vials were combined together to perform a small volume HIAC assay.

Figures 6A, 6B:
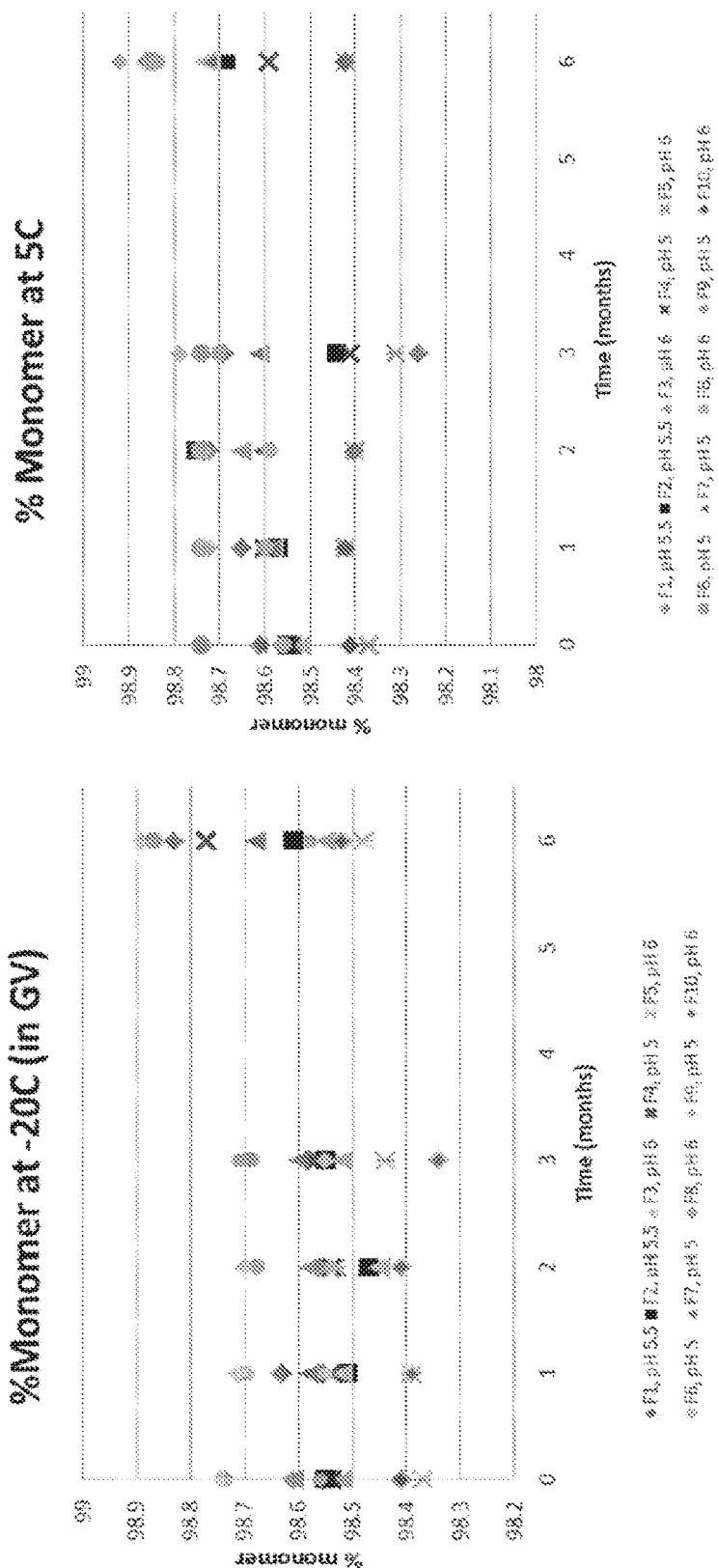
FIGS. 6A-6D are a series of graphs showing stability of α-PDL1 formulations stored at −20° C. or 5° C. for up to 6 months in a glass vial (GV).
Figures 6C, 6D:
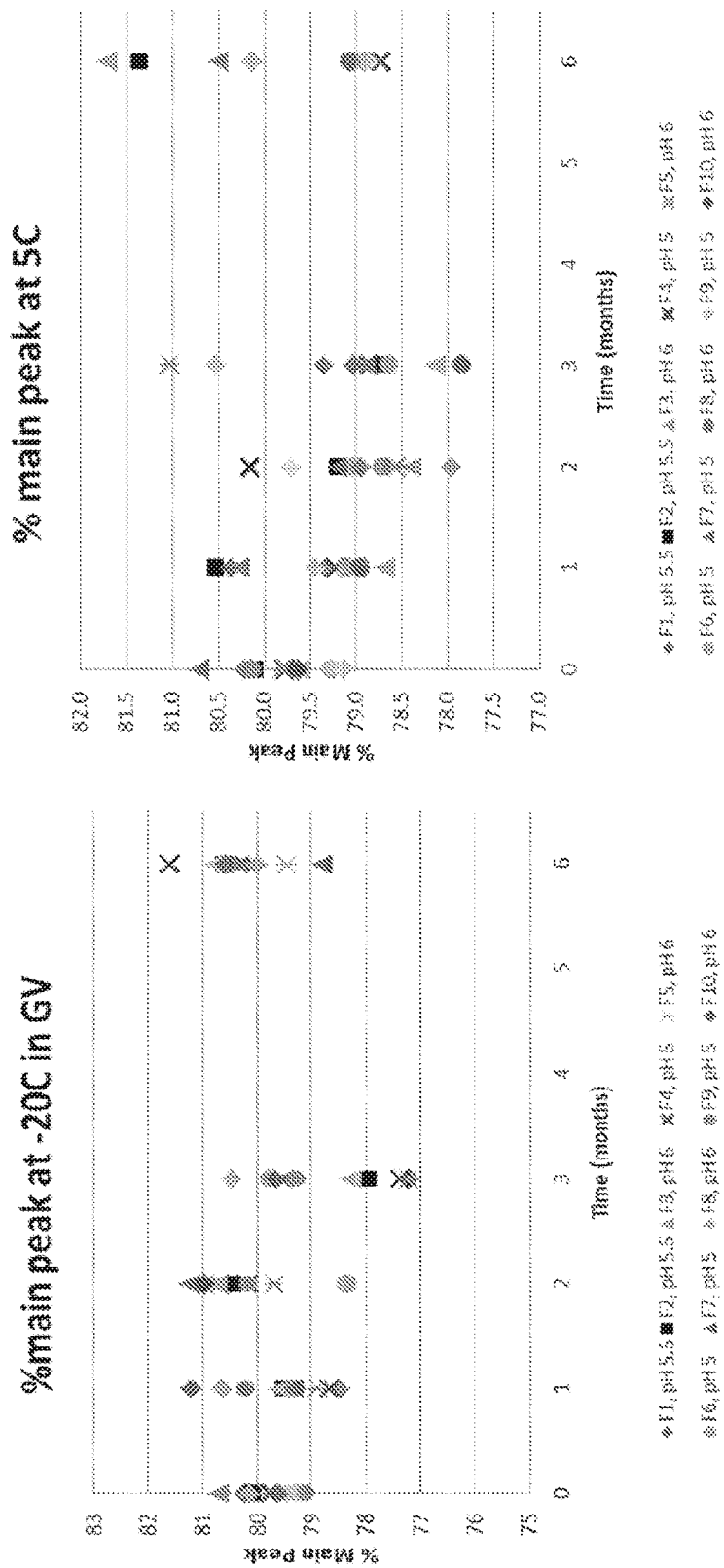

Stability of the formulations was further investigated with a freeze thaw experiment. Formulations F1 through F10 (Table 4) were subjected to either five freeze thaw cycles during storage at −20° C. or were stored at an elevated storage temperature of 5° C. from 0 to 6 months and subsequently analyzed by SEC and ICIEF for percentage of α-PDL1 monomer (FIGS. 6A and B) and percentage of main peak in formulation (FIGS. 6C and D). No significant change in percent monomer and percent main peak was observed after the freeze thaw cycles and storage at the indicated time points.

The Drug Substance stability in the F2 formulation (Table 4) was assessed by conducting five freeze thaw cycles during storage in a stainless steel minican at −20° C. for up to 6 months followed by stability measurement by CAC, SEC, and ICIEF (Table 7). No change was observed after 6 months storage at −20° C.

TABLE 7

Drug Substance stability in a stainless steel minican stored at −20° C.

| Time Points | F/T Cycles | Q12005 CAC Clarity | Q12589 SEC (% monomer) | Q12631 ICIEF (% main peak) |
|---|---|---|---|---|
| T0 | 0 | CL/SY | 98.6 | 80.1 |
| 1 M | 1 | CL/SY | 98.6 | 79.1 |
| 2 M | 2 | CL/SY | 98.7 | 80.2 |
| 3 M | 3 | CL/SY | 98.8 | 80.9 |
| 6 M | 5 | CL/SY | 98.6 | 80.2 |

Note:
F/T = freeze/thaw; SY = slightly yellow; CL = clear.

The Drug Substance stability in a formulation containing 100 mg/mL α-PDL1, 20 mM histidine acetate, 120 mM sucrose, 0.04% PS20, pH 5.6 was assessed by conducting three freeze thaw cycles followed by storage in a stainless steel minican or hastelloy minican at −20° C., 5° C., or 25° C. for up to 3 months followed by stability measurement by SEC (FIGS. 7A and B). No difference was observed between storage in stainless steel and hastelloy minicans at pH 5.6. The Drug Substance was stable for up to 3 months at −20° C. after three freeze thaw cycles. Despite slight differences in stainless steel and hastelloy minicans, both were appropriate for use for drug substance storage.

Figure 8A:
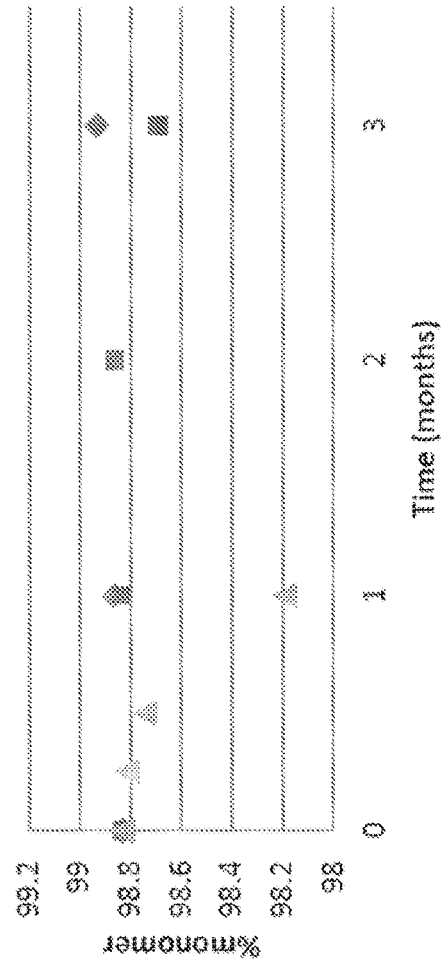
FIG. 8A and FIG. 8B are a series of graphs showing stability of an α-PDL1 formulation storage in a 20 cc vial.
Figure 8B:
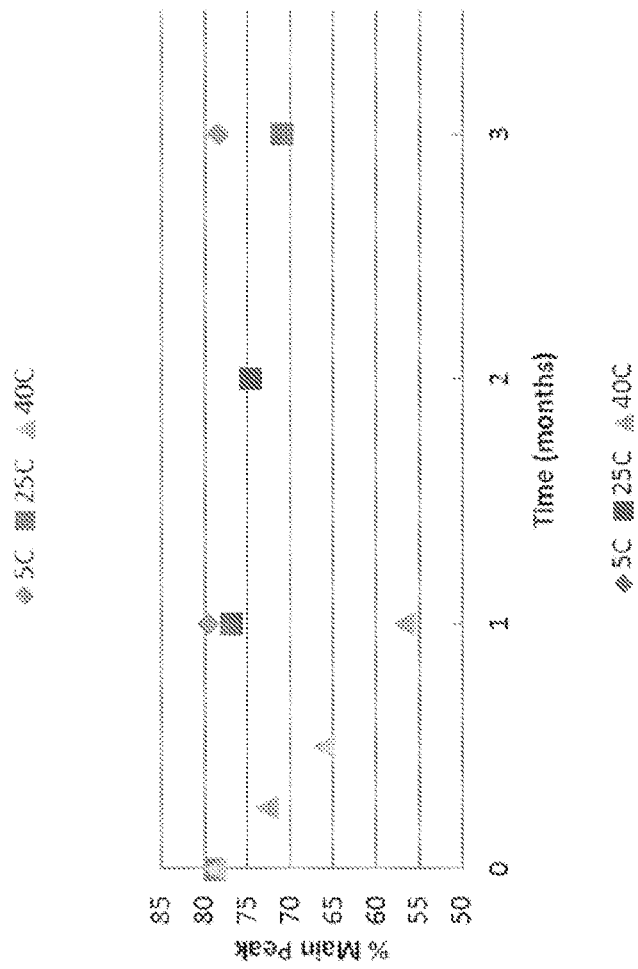

The Drug Product stability in a formulation containing 50 mg/mL α-PDL1, 20 mM histidine acetate, 120 mM sucrose, 0.04% PS20, pH 5.6 was assessed when stored as 16 mL fill in a 20 cc vial at −5° C., 25° C., or 40° C. for up to 3 months followed by stability measurement with SEC and ICIEF (FIGS. 8A and B). No change was observed at 5° C. after three months of storage. The pH 5.6 degradation rate per month at 40° C. was 0.66% and 22% by SEC and ICIEF analysis, respectively.

Assessment of the buffer in the F12 formulation indicated that the sodium acetate buffer provided similar protein stability as histidine acetate buffer, based on main peak degradation rates measured by SE-HPLC and ICIEF (Table 8). The two formulations tested were 50 mg/ml, α-PDL1 in 20 mM L-histidine acetate, 120 mM sucrose, and 0.04% (w/v) polysorbate 20 at pH 5.5 and 0 mg/mL α-PDL1 in 20 mM sodium acetate, 120 mM sucrose, and 0.04% (w/v) polysorbate 20 at pH 5.5.

TABLE 8

Zero-Order Degradation Rates of α-PDL1 for ICIEF and SE-HPLC Main Peak in Histidine Acetate and Sodium Acetate buffers at 40° C.

| α-PDL-1 Concentration (mg/mL) | Rate of % Main Peak Decrease per Month | |
|---|---|---|
| | ICIEF | SE-HPLC |
| Histidine Acetate | 23 | 0.67 |
| Sodium Acetate | 21 | 0.74 |

Note:
All formulations were stored for up to 1 month at 40° C.

Figure 1B:
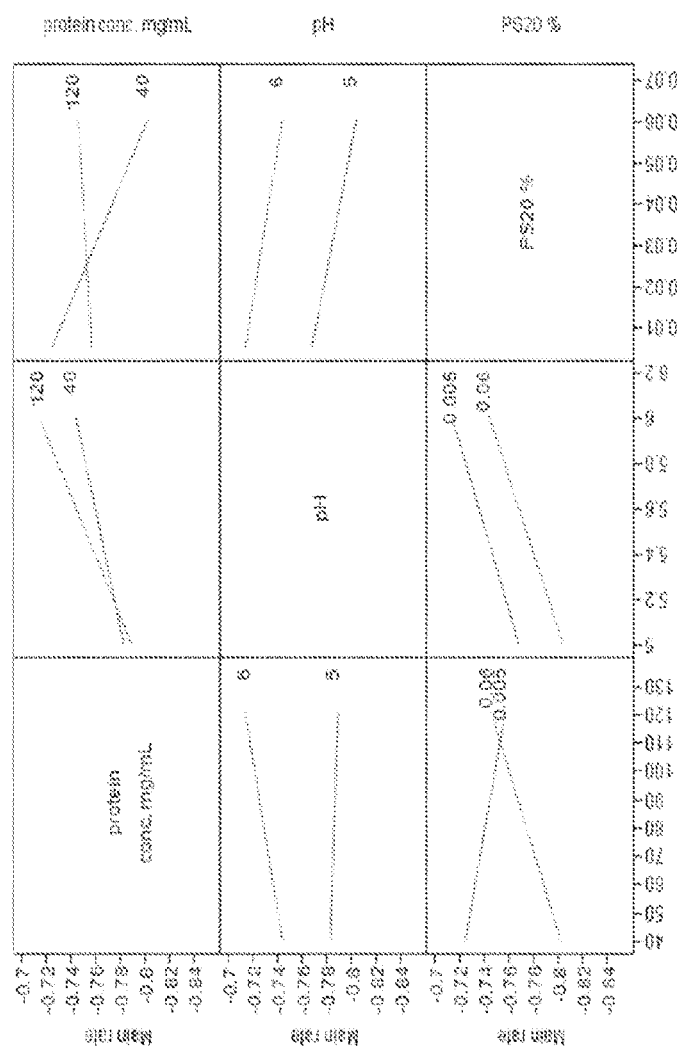
Figures 2A, 2B:
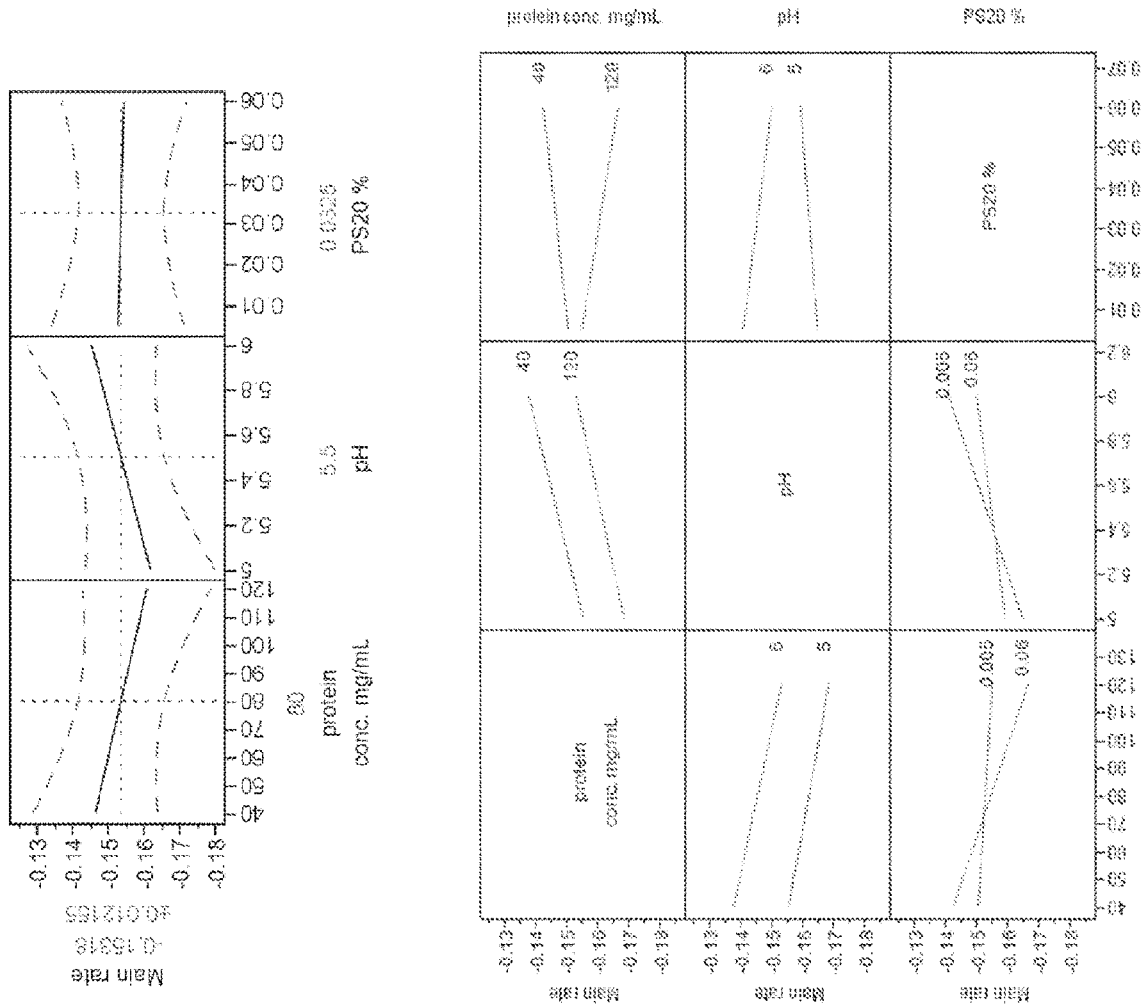
FIG. 2A and FIG. 2B are a series of graphs showing statistical analysis of stability data of α-PDL1 formulations at 25° C. by ICIEF using JMP software.
Figures 3A, 3B:
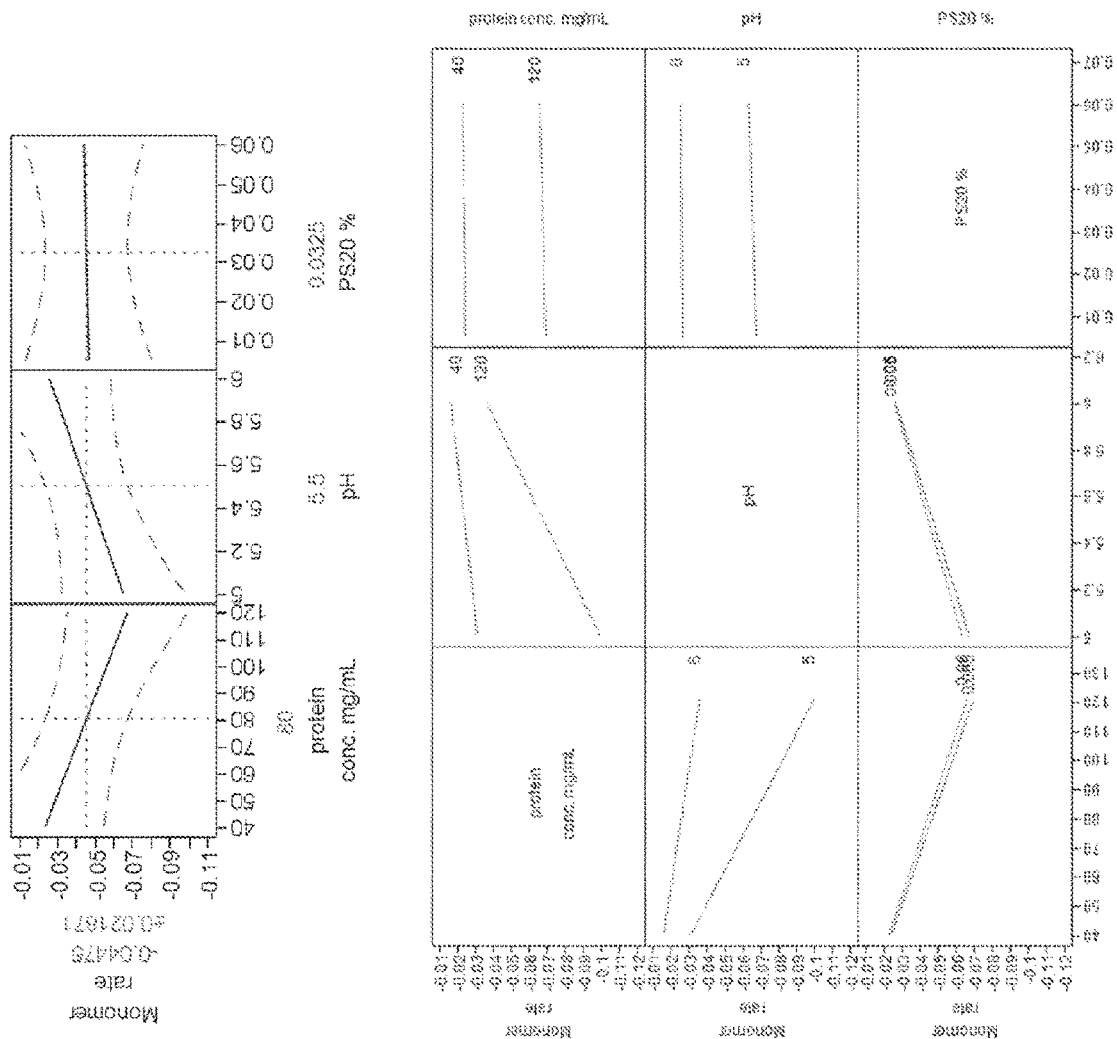
FIG. 3A and FIG. 3B are a series of graphs showing statistical analysis of stability data of α-PDL1 formulations at 40° C. by SE-HPLC using JMP software.
Figures 4A, 4B:
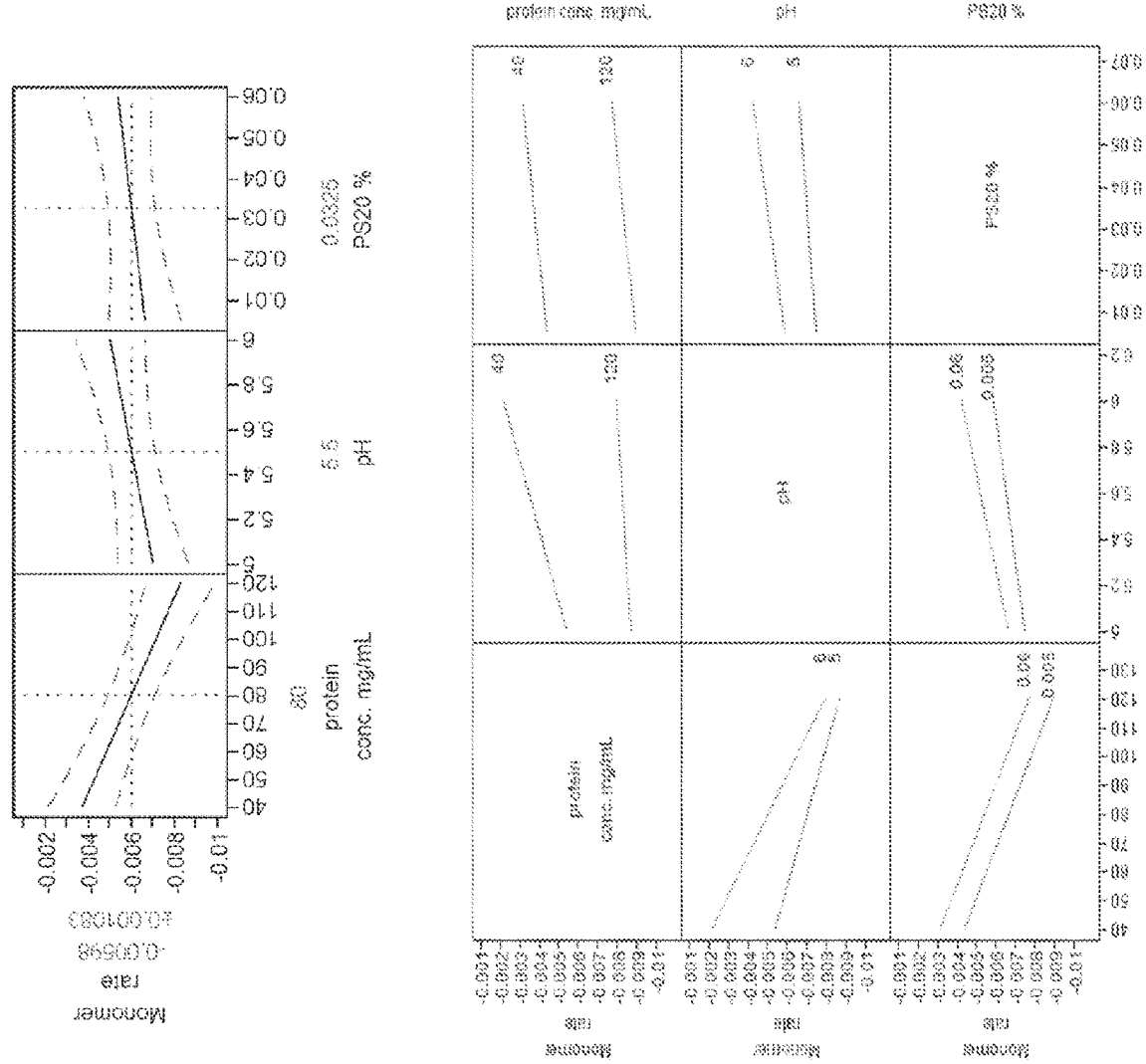
FIG. 4A and FIG. 4B are a series of graphs showing statistical analysis of stability data of α-PDL1 formulations at 25° C. by SE-HPLC using JMP software.

Overall, the DoE designed stability studies revealed that at 40° C. no significant impact of concentration on main peak loss was observed by ICIEF, while lower pH has a slightly faster main peak rate loss (FIGS. 1A-B). At 40° C. no significant interactions were observed by SE-HPLC either, however, the higher concentration formulations show a faster monomer loss (FIGS. 3A-B). It was also found that lower pH has a faster monomer rate loss. Similar results were observed at 25° C. (FIGS. 2A-B and FIGS. 4A-B). The statistical analysis revealed no practically meaningful interactions (linkage) between any of the tested formulation parameters.

Agitation and Thermal Stress Studies

Stability of the drug product in the presence of increasing concentrations of PS20 when undergoing agitation stress in glass vials was investigated. A formulation containing 57 mg/mL in 20 mM histidine acetate, 120 mM sucrose, pH 5.5 was assessed in a 1 mL fill in 2 cc glass vials with various concentrations of PS20 ranging from 0.005% to 0.06%. Glass vials were agitated at 70 rpm for 3 days at room temperature prior to measurement of stability by SEC (FIG. 9A) and turbidity (FIG. 9B) measurements. Formulation with PS20 levels between 0.005-0.06% had no change in stability during agitation. However, formulations lacking PS20 showed an increase in monomer loss due to an HMWS increase. In this experiment, 0.005% PS20 was sufficient to protect protein from agitation stress in glass vials.

Figure 10:
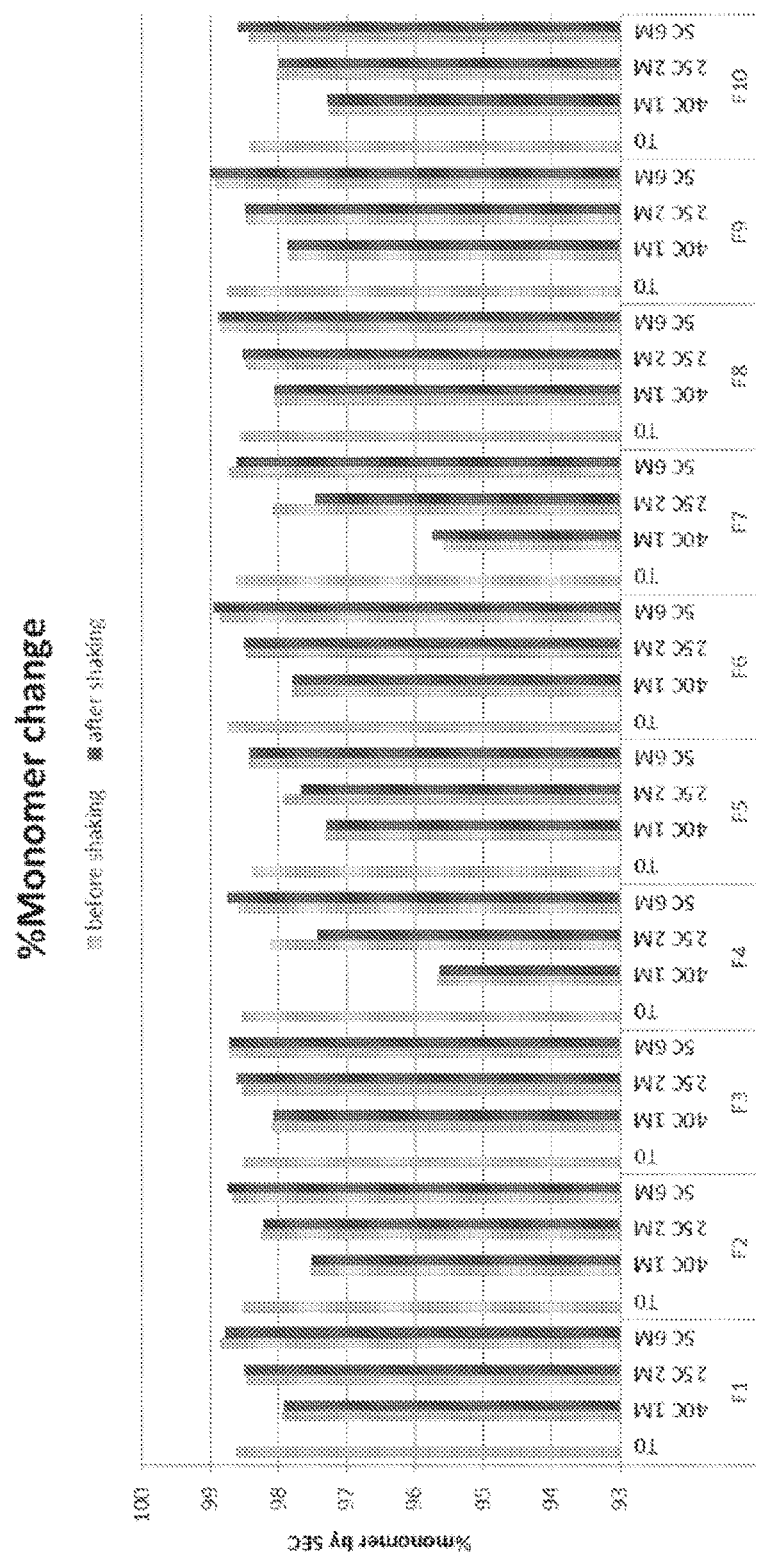
FIG. 10 is a graph showing stability of α-PDL1 formulations stored in glass vials for a period of time at the indicated temperatures and then subjected to agitation. Percent monomer change in formulations was measured by SEC.

Stability of the drug product formulations (Table 4) when stored at various temperature and time and then undergoing agitation stress in glass vials was investigated. Formulations F1-F10 were each assessed in a 1 mL fill in 2 cc glass vial. Glass vials were agitated at 70 rpm for 1 day at room temperature prior to measurement of stability by SEC (FIG. 10). In this experiment, agitation has no impact on the stability of drug product when stored for a length of time at 40° C., 25° C. or 5° C.

In order to support IV bag transportation which often occurs in hospital settings, an IV bag agitation study was performed with α-PDL1 formulated in 20 mM histidine acetate, 240 mM sucrose, pH 5.5 with 0.005%-0.02% (w/v) polysorbate 20. The most commonly available 250 mL polyvinyl chloride (PVC) or polyolefin (PO) IV bags containing isotonic sodium chloride solution (0.9% NaCl) were evaluated by injecting 400-600 mg of α-PDL1 solutions and agitated using orbital shaker at 100 rpm at 5° C. for up to 6 hours. The results of the study supported weight-based dosing and demonstrated that a minimum of 0.015% (w/v) of polysorbate 20 in protein solution is needed in order to prevent visible particles formation (related to protein precipitation) during transportation (Table 9). In addition, to mitigate the risk of polysorbate 20 degradation over shelf life, the polysorbate 20 concentration was increased from 0.02% (w/v) to 0.04% (w/v).

TABLE 9

IV Bag Agitation Study with Different Amount of PS20 in α-PDL1 Drug Product

| % PS20 in DP | Samples | CAC | SE-HPLC % HMWS | SE-HPLC % Monomer | Subvisible particles (ppmL) ≥10 um | Subvisible particles (ppmL) ≥25 um |
|---|---|---|---|---|---|---|
| 0.005% | 250 mL PO bag, T0 | CO, CL, PFVP | NT | NT | NT | NT |
| | 250 mL PO bag, agitation at 5° C. for 2 hours | Visible particles observed Experiment stopped | NT | NT | NT | NT |
| | 250 mL PVC bag, T0 | CO, CL, PFVP | NT | NT | NT | NT |
| | 250 mL PVC bag, agitation at 5° C. for 2 hours | Visible particles observed Experiment stopped | NT | NT | NT | NT |
| 0.01% | 250 mL PO bag, T0 | CO, CL, PFVP | NT | NT | NT | NT |
| | 250 mL PO bag, agitation at 5° C. for 2 hours | Visible particles observed Experiment stopped | NT | NT | NT | NT |
| | 250 mL PVC bag, T0 | CO, CL, PFVP | NT | NT | NT | NT |
| | 250 mL PVC bag, agitation at 5° C. for 4 hours | CO, CL, PFVP | NT | NT | NT | NT |
| 0.015% | 250 mL PO bag, T0 | CO, CL, PFVP | 1.2 | 98.8 | 21 | 2 |
| | 250 mL PO bag, agitation at 5° C. for 4 hours | CO, CL, PFVP | 1.3 | 98.7 | 195 | 19 |
| | 250 mL PVC bag, T0 | CO, CL, PFVP | 1.2 | 98.8 | 16 | 0 |
| | 250 mL PVC bag, agitation at 5° C. for 4 hours | CO, CL, PFVP | 1.2 | 98.8 | 24 | 2 |

Note:

All formulations 50 mg/mL α-PDL1 in 20 mM L-histidine acetate, 240 mM sucrose at pH 5.5.

Analysis was performed using SE-HPLC.

NT = not tested; CAC = color, appearance, and clarity; CO = Colorless; CL = Clear; PFVP = Practically Free of Visible Particulates.

Stability Assessment of α-PDL1 Formulations

Figure 11A:
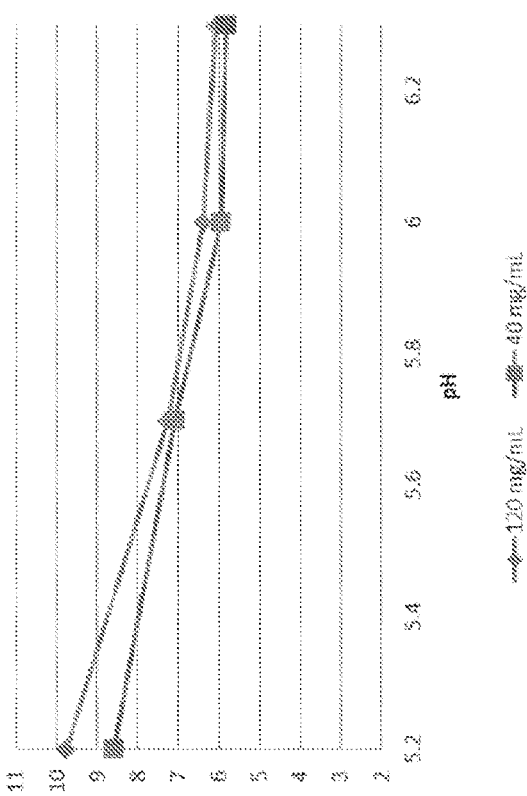
FIG. 11A and FIG. 11B are a series of graphs showing comparability of α-PDL1 loss rate per week with increasing pH.
Figure 11B:
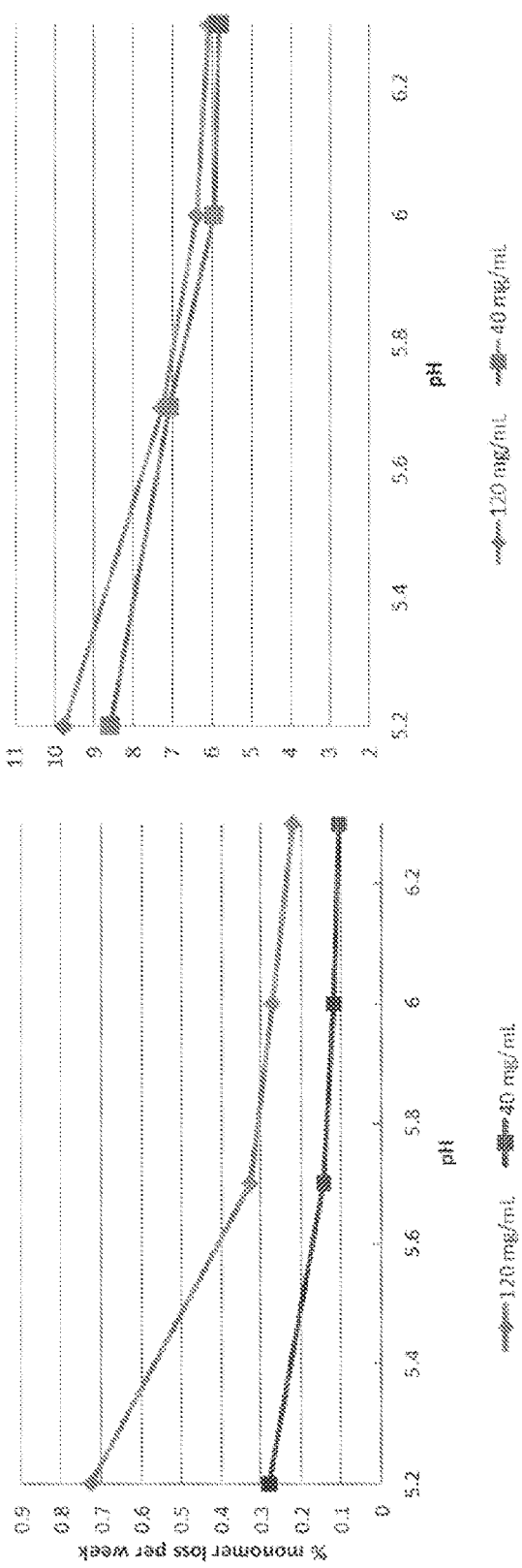

An additional pH screen was conducted on the materials produced from a Master Cell Bank and a Working Cell Bank across a pH range of 5.2 to 6.3 in a formulation containing 20 mM histidine acetate, 120 mM sucrose, and 0.04% PS20 (Table 10). Analysis by SE-HPLC and ICIEF showed that pH 5.7-6.3 was chemically and physically fairly stable and an allowed range of pH 5.5-6.3 in the formulation was appropriate (FIGS. 11A and B). Higher pH reduced monomer and main peak degradation rates, with rates flattening out between about pH 5.7 and 6.3.

TABLE 10 pH screen of Formulations

| Concentration (mg/mL) | pH | Container | Temperature (° C.) | Time Points |
|---|---|---|---|---|
| 120 | 5.2, 5.7, 6.0, 6.3 | 1 mL fill in 2 cc vial | 40 | T0, 1 week, 2 week, 1 month |
| 40 | 5.2, 5.7, 6.0, 6.3 | 1 mL fill in 2 cc vial | 40 | T0, 1 week, 2 week, 1 month |

The effect of formulation excipients on tryptophan (W) and methionine (M) oxidation in α-PDL1 formulations was investigated. Peptide mapping showed there was no significant oxidation increase. Formulations containing 20 mM histidine acetate, 120 mM sucrose, 0.04% PS20 with a solution pH of 5.8 showed no apparent tryptophan and methionine oxidation increase when the formulation was stored for one month at elevated temperatures for either the Drug Product or Drug Substance (Table 11).

TABLE 11

Percentage of Trp, $M^{253}$ and $M^{429}$ oxidation in Selected Formulations by Peptide Map

| | % Oxidation | | | | |
|---|---|---|---|---|---|
| Sample | W CDR H2 | W CDR H4 | W CDR H10 | $M^{253}$ | $M^{429}$ |
| DP, 50 mg/mL, T 0 | 0.35 | 0.26 | 0.12 | 4.86 | 0.92 |
| DP, 50 mg/mL, 40° C., T = 1 M | 0.63 | 0.26 | 0.31 | 5.85 | 1.10 |
| DS, 100 mg/mL, SS, 25° C., T = 1 M | 0.52 | 0.27 | 0.28 | 5.61 | 1.17 |

Note:
All formulations of α-PDL1 contained 20 mM L-histidine acetate, 120 mM sucrose, 0.04% PS20, pH 5.8.

Based on the results from these formulation studies and statistical analysis, a liquid formulation consisting of 60 mg/mL α-PDL1 in 20 mM histidine acetate, 120 mM sucrose, 0.04% polysorbate 20 with a target pH 5.8 was selected for clinical studies.

The dosage for clinical trials will be conducted as a flat dose of 1200 mg α-PDL1 per patient. A vial configuration of nominal 20 mL fill (1200 mg α-PDL1) in a 20 cc glass vial was selected to meet the target product profile.

Freeze/thaw studies were conducted with the intended formulation containing 60 mg/mL α-PDL1 in 20 mM L-histidine acetate, 120 mM sucrose, and 0.02% (w/v) polysorbate 20 at pH 5.8. Assay results after five freeze/thaw cycles confirmed 120 mM of sucrose protected α-PDL1 from freeze/thaw-induced aggregation (Table 12). Similarly long-term stability of the intended liquid formulation indicated that it is stable for over 6 months at 2-8° C. (Table 13). Continuous monitoring over 36 months is underway for this formulation. Target formulation and tested study ranges for α-PDL1 Drug Substance and Drug Product are shown in Table 14.

TABLE 12

Representative Freeze/Thaw Stability Data for α-PDL1 Drug Substance Development Batch

| No. Freeze-Thaw Cycles | CAC | Strength (mg/mL) | pH | ICIEF Acidic Region (area %) | ICIEF Main Peak (area %) | ICIEF Basic Region (area %) | SE-HPLC Sum of HMW Forms (area %) |
|---|---|---|---|---|---|---|---|
| NA | CL/SY/PFVP | 60.1 | 5.9 | 19 | 78 | 3 | 0.5 |
| 5 | CL/SY/PFVP | 62.0 | 5.9 | 20 | 77 | 3 | 0.5 |

| No. Freeze-Thaw Cycles | SE-HPLC Monomer (area %) | SE-HPLC Sum of LMW Forms (area %) | CE SDS NGS (non-reduced) Sum of Pre-Peaks (% CPA) | CE SDS NGS (non-reduced) Main Peak (% CPA) | CE SDS NGS (non-reduced) Sum of Post-Peaks (% CPA) | Potency (% specific activity) |
|---|---|---|---|---|---|---|
| NA | 99.4 | 0.1 | 2.9 | 97.0 | 0.1 | 107 |
| 5 | 99.4 | 0.1 | 2.7 | 97.1 | 0.2 | 111 |

Note:
Batch PP400L-02142013 contains 60 mg/mL α-PDL1 in 20 mM L-histidine acetate, 120 mM sucrose, and 0.04% (w/v) polysorbate 20 at pH 5.8.
CL = Clear; SY = Slightly Yellow; PFVP = Practically Free of Visible Particulates; NA = not applicable, ICIEF = imaged capillary isoelectric focusing; CE-SDS = capillary electrophoresis sodium dodecyl sulfate; HMW = high molecular weight; LMW = low molecular weight.

TABLE 13

Stability Data for α-PDL1 Drug Development Batch

| Temp (° C.) | Time (days/ months) | CAC | pH | Strength (mg/mL) | Imaged cIEF | | | SE-HPLC Sum of HMW Forms (area %) |
|---|---|---|---|---|---|---|---|---|
| | | | | | Acidic Region (area %) | Main Peak (area %) | Basic Region (area %) | |
| NA | T = 0/0 | SY/CL/PFVP | 5.9 | 59.9 | 18.1 | 78.9 | 2.9 | 0.6 |
| 5 | 30/1 | SY/CL/PFVP | 5.9 | 59.9 | 18.3 | 78.6 | 3.1 | 0.6 |
| 5 | 61/2 | SY/CL/PFVP | 5.9 | 61.7 | 18.4 | 78.9 | 2.7 | 0.7 |
| 5 | 91/3 | SY/CL/PFVP | 5.9 | 61.7 | 17.1 | 80.1 | 2.8 | 0.7 |
| 5 | 183/6 | SY/CL/PFVP | 5.9 | 60.8 | 18.4 | 78.6 | 3.0 | 0.7 |

| Temp (° C.) | SE-HPLC | | CE SDS NGS (non-reduced) | | | Potency (% specific activity) | Sub-Visible Particles[a] (ppmL) | |
|---|---|---|---|---|---|---|---|---|
| | Monomer Peak (area %) | Sum of LMW Forms (area %) | Sum of Pre-Peaks (% CPA) | Main Peak (% CPA) | Sum of Post-Peaks (% CPA) | | ≥10 um | ≥25 um |
| NA | 99.3 | 0.1 | 2.7 | 97.0 | 0.3 | 99 | 37 | 30 |
| 5 | 99.3 | 0.1 | 2.7 | 96.9 | 0.4 | NT | 26 | 2 |
| 5 | 99.3 | 0.1 | 2.8 | 96.9 | 0.4 | NT | 3 | 0 |
| 5 | 99.2 | 0.1 | 2.7 | 97.0 | 0.4 | 102 | 18 | 3 |
| 5 | 99.2 | 0.1 | 3.1 | 96.5 | 0.4 | 101 | 3 | 0 |

Batch PP400L-02142013-DP contains 60 mg/mL α-PDL1 in 20 mM L-histidine acetate, 120 mM sucrose, and 0.04% (w/v) polysorbate 20 at pH 5.8.
NA = not applicable; CAC = color, appearance, and clarity; SY = slightly yellow, CL = clear, PFVP = practically free of visible particulates; HMW = high molecular weight; LMW = low molecular weight; ICIEF = imaged capillary isoelectric focusing; CE-SDS = capillary electrophoresis sodium dodecyl sulfate, NT = not tested.

TABLE 14

Target formulation and tested study ranges for α-PDL1 drug substance and drug product

| Parameter | Target | Tested Formulation Range |
|---|---|---|
| α-PDL1 Concentration | 60 mg/mL | 40-120 mg/mL |
| L-Histidine Acetate Concentration | 20 mM | 20 mM |
| Solution pH | 5.8 | 5.0-6.0 |
| Sucrose Concentration | 120 mM | 0-240 mM |
| Polysorbate 20 Concentration (w/v) | 0.04% | 0.005%-0.06%[a] |

Since α-PDL1 drug product (60 mg/mL) will be administered by infusion after dilution in isotonic sodium chloride solution (0.9% NaCl), compatibility and stability of the active ingredient was tested under the following simulated preparation and administration conditions: 1) Dilution of α-PDL1 drug product in infusion bags containing 0.9% NaCl in the range of 2.4-9.6 mg/ml (nominal concentration after dilution) to cover the dose range in the clinical study; 2) Short-term exposure to infusion bags containing isotonic sodium chloride solution (bag product-contact surface material consisting of PVC or Polyolefin); 3) Use of IV infusion lines with (product-contacting surfaces of PVC or Polyolefin); and 4) Use of 0.2 μm in-line filters (filter membrane of PES).

Samples were tested after 24 hours of storage at 2° C.-8° C. or after 24 hours at 30° C. with exposure to diffused light. The samples were tested using appropriate stability indicating methods including: purity by SE-HPLC and ICIEF, protein concentration (by UV), subvisible particles by light obscuration, color, clarity/opalescence, and pH (Table 15).

TABLE 15

Stability of α-PDL1 diluted and stored at 5° C. or 30° C. for 24 hours in 0.9% NaCl infusion bags with and without 0.2 μm in-line filters

| Sample | CAC | Strength (mg/mL) | Turbidity A₃₅₀ | ICIEF % Acidic | ICIEF % Main Peak | ICIEF % Basic | SE-HPLC % HMWS | SE-HPLC % Monomer | SE-HPLC % LMWS | pH | Particulates (counts/mL) ≥10 um | Particulates (counts/mL) ≥25 um |
|---|---|---|---|---|---|---|---|---|---|---|---|---|
| 2.4 mg/mL in PVC bag, T0 | CL, CO, PFVP | 2.1 | 0.01 | 19.5 | 75.7 | 4.8 | 0.4 | 99.5 | 0.1 | 5.9 | 25 | 1 |
| 2.4 mg/mL in PVC bag, t = 5° C., 24 hrs before infusion | CL, CO, PFVP | 2.2 | 0.02 | 19.6 | 75.5 | 4.9 | 0.4 | 99.5 | 0.1 | 5.8 | 32 | 0 |
| 2.4 mg/mL in PVC bag, t = 30° C., 24 hrs before infusion | CL, CO, PFVP | 2.2 | 0.01 | 19.3 | 76.6 | 4.1 | 0.3 | 99.5 | 0.1 | 5.8 | 32 | 0 |
| 2.4 mg/mL in PVC bag, t = 5° C., 24 hrs, passing through infusion set without in-line filter | CL, CO, PFVP | 2.1 | 0.04 | 19.5 | 76.4 | 4.1 | 0.4 | 99.5 | 0.1 | 5.8 | 44 | 1 |
| 2.4 mg/mL in PVC bag, t = 5° C., 24 hrs, passing through infusion set with in-line filter | CL, CO, PFVP | 2.1 | 0.01 | 19.3 | 76.7 | 4.1 | 0.3 | 99.5 | 0.1 | 5.9 | 4 | 0 |
| 2.4 mg/mL in PVC bag, t = 30° C., 24 hrs passing through infusion set without in-line filter | CL, CO, PFVP | 2.1 | 0.02 | 20.0 | 75.7 | 4.3 | 0.3 | 99.6 | 0.1 | 5.9 | 29 | 0 |
| 2.4 mg/mL in PVC bag, t = 30° C., 24 hrs passing through infusion set with in-line filter | CL, CO, PFVP | 2.0 | 0.04 | 19.5 | 76.4 | 4.1 | 0.3 | 99.6 | 0.1 | 6.0 | 5 | 0 |

| Sample | CAC | Strength (mg/mL) | Turbidity A₃₅₀ | ICIEF % Acidic | ICIEF % Main Peak | ICIEF % Basic | SE-HPLC % HMWS | SE-HPLC % Monomer | SE-HPLC % LMWS | pH | Particulates (ppmL) ≥10 um | Particulates (ppmL) ≥25 um |
|---|---|---|---|---|---|---|---|---|---|---|---|---|
| 2.4 mg/mL in PO bag, T0 | CL, CO, PFVP | 2.1 | 0.01 | 18.6 | 77.3 | 4.1 | 0.4 | 99.5 | 0.1 | 6.1 | 5 | 0 |
| 2.4 mg/mL in PO bag, t = 5° C., 24 hrs before infusion | CL, CO, PFVP | 2.1 | 0.03 | 17.8 | 77.8 | 4.4 | 0.4 | 99.5 | 0.1 | 5.9 | 3 | 0 |
| 2.4 mg/mL in PO bag, t = 30° C., 24 hrs before infusion | CL, CO, PFVP | 2.1 | 0.02 | 20.6 | 75.3 | 4.1 | 0.3 | 99.5 | 0.1 | 5.9 | 8 | 0 |
| 2.4 mg/mL in PO bag, t = 5° C., 24 hrs, passing through infusion set without in-line filter | CL, CO, PFVP | 2.1 | 0.01 | 20.5 | 75.3 | 4.2 | 0.4 | 99.5 | 0.1 | 5.9 | 48 | 0 |
| 2.4 mg/mL in PO bag, t = 5° C., 24 hrs, passing through infusion set with in-line filter | CL, CO, PFVP | 2.1 | 0.02 | 21.0 | 74.8 | 4.3 | 0.4 | 99.5 | 0.1 | 5.9 | 1 | 0 |
| 2.4 mg/mL in PO bag, t = 30° C., 24 hrs passing through infusion set without in-line filter | CL, CO, PFVP | 2.1 | 0.01 | 18.7 | 76.9 | 4.4 | 0.3 | 99.5 | 0.1 | 5.9 | 22 | 0 |
| 2.4 mg/mL in PO bag, t = 30° C., 24 hrs passing through infusion set with in-line filter | CL, CO, PFVP | 2.1 | 0.01 | 21.2 | 73.9 | 4.9 | 0.4 | 99.5 | 0.1 | 6.0 | 0 | 0 |

TABLE 15-continued

Stability of α-PDL1 diluted and stored at 5° C. or 30° C. for 24 hours in 0.9% NaCl infusion bags with and without 0.2 μm in-line filters

| Sample | CAC | Strength (mg/mL) | Turbidity A350 | ICIEF % Acidic | % Main Peak | % Basic | % HMWS | % Monomer | % LMWS | pH | Particulates (counts/mL) ≥10 um | ≥25 um (ppmL) |
|---|---|---|---|---|---|---|---|---|---|---|---|---|
| 9.6 mg/mL in PVC bag, T0 | CL, CO, PFVP | 8.7 | 0.05 | 18.3 | 77.3 | 4.4 | 0.4 | 99.5 | 0.1 | 5.9 | 35 | 0 |
| 9.6 mg/mL in PVC bag, t = 5° C., 24 hrs before infusion | CL, CO, PFVP | 8.6 | 0.03 | 19.0 | 76.8 | 4.2 | 0.4 | 9.5 | 0.1 | 5.9 | 6 | 1 |
| 9.6 mg/mL in PVC bag, t = 30° C., 24 hrs before infusion | CL, CO, PFVP | 8.5 | 0.05 | 18.9 | 77.0 | 4.1 | 0.4 | 99.5 | 0.2 | 5.9 | 10 | 0 |
| 9.6 mg/mL in PVC bag, t = 5° C., 24 hrs, passing through infusion set without in-line filter | CL, CO, PFVP | 8.8 | 0.03 | 19.2 | 76.4 | 4.4 | 0.3 | 99.6 | 0.1 | 6.0 | 29 | 0 |
| 9.6 mg/mL in PVC bag, t = 5° C., 24 hrs, passing through infusion set with in-line filter | CL, CO, PFVP | 8.7 | 0.06 | 19.0 | 77.1 | 3.9 | 0.3 | 99.6 | 0.1 | 5.9 | 18 | 0 |
| 9.6 mg/mL in PVC bag, t = 30° C., 24 hrs, passing through infusion set without in-line filter | CL, CO, PFVP | 8.1 | 0.04 | 19.1 | 76.6 | 4.3 | 0.4 | 99.5 | 0.2 | 6.0 | 8 | 0 |
| 9.6 mg/mL in PVC bag, t = 30° C., 24 hrs, passing through infusion set with in-line filter | CL, CO, PFVP | 8.8 | 0.04 | 19.6 | 76.4 | 4.0 | 0.3 | 99.6 | 0.1 | 5.9 | 19 | 2 |

| Sample | CAC | Strength (mg/mL) | Turbidity A350 | % Acidic | % Main Peak | % Basic | % HMWS | SE-HPLC % Monomer | % LMWS | pH | Particulates (counts/mL) ≥10 um | ≥25 um |
|---|---|---|---|---|---|---|---|---|---|---|---|---|
| 9.6 mg/mL in PO bag, T0 | CL, CO, PFVP | 8.4 | 0.03 | 18.6 | 78.0 | 3.4 | 0.4 | 99.5 | 0.1 | 5.8 | 33 | 2 |
| 9.6 mg/mL in PO bag, t = 5° C., 24 hrs before infusion | CL, CO, PFVP | 8.6 | 0.04 | 19.2 | 76.4 | 4.4 | 0.4 | 99.5 | 0.1 | 5.9 | 32 | 0 |
| 9.6 mg/mL in PO bag, t = 30° C., 24 hrs before infusion | CL, CO, PFVP | 8.7 | 0.04 | 19.3 | 76.7 | 4.0 | 0.4 | 99.5 | 0.1 | 5.9 | 18 | 0 |
| 9.6 mg/mL in PO bag, t = 5° C., 24 hrs, passing through infusion set without in-line filter | CL, CO, PFVP | 8.5 | 0.05 | 19.8 | 75.8 | 4.5 | 0.3 | 99.5 | 0.1 | 5.9 | 38 | 1 |
| 9.6 mg/mL in PO bag, t = 5° C., 24 hrs, passing through infusion set with in-line filter | CL, CO, PFVP | 8.2 | 0.04 | 18.6 | 77.2 | 4.3 | 0.4 | 99.5 | 0.1 | 5.8 | 8 | 0 |
| 9.6 mg/mL in PO bag, t = 30° C., 24 hrs, passing through infusion set without in-line filter | CL, CO, PFVP | 8.5 | 0.03 | 19.4 | 76.0 | 4.6 | 0.4 | 99.5 | 0.1 | 5.9 | 48 | 7 |
| 9.6 mg/mL in PO bag, t = 30° C., 24 hrs, passing through infusion set with in-line filter | CL, CO, PFVP | 8.0 | 0.05 | 19.7 | 76.1 | 4.2 | 0.3 | 99.5 | 0.1 | 5.8 | 10 | 0 |

CO = Colorless,
CL = Clear,
PFVP = Practically Free of Visible Particulates,
$A_{350}$ = absorbance at 350 nm

TABLE 16

Agitation Stability of α-PDL1 diluted in 0.9% NaCl infusion bags at 5° C. for up to 6 hours

| Sample | CAC | Strength (mg/mL) | Turbidity $A_{350}$ | ICIEF % Acidic | ICIEF % Main Peak | ICIEF % Basic | SE-HPLC % HMWS | SE-HPLC % Monomer | SE-HPLC % LMWS | pH | Particulates (counts/mL) ≥10 um | Particulates (counts/mL) ≥25 um |
|---|---|---|---|---|---|---|---|---|---|---|---|---|
| 2.4 mg/mL in PO bag, T0 | CL, CO, PFVP | 2.13 | 0.02 | 17.5 | 79.1 | 3.4 | 0.8 | 99.1 | 0.1 | 5.9 | 3 | 0 |
| 2.4 mg/mL in PO bag, 2 hr agitation | CL, CO, PFVP | 2.09 | 0.01 | 17.1 | 79.8 | 3.1 | 0.8 | 99.1 | 0.1 | 5.9 | 113 | 2 |
| 2.4 mg/mL in PO bag, 4 hr agitation | CL, CO, PFVP | 2.12 | 0.02 | 17.3 | 79.6 | 3.1 | 0.8 | 99.1 | 0.1 | 5.9 | 31 | 0 |
| 2.4 mg/mL in PO bag, 6 hr agitation | CL, CO, PFVP | 2.02 | 0.02 | 16.8 | 79.6 | 3.6 | 0.8 | 99.1 | 0.1 | 5.9 | 4 | 1 |
| 2.4 mg/mL in PVC bag, T0 | CL, CO, PFVP | 2.42 | 0.02 | 17.9 | 78.6 | 3.5 | 0.8 | 99.1 | 0.1 | 5.9 | 6 | 0 |
| 2.4 mg/mL in PVC bag, 2 hr agitation | CL, CO, PFVP | 2.04 | 0.02 | 17.6 | 79.2 | 3.2 | 0.8 | 99.1 | 0.1 | 5.9 | 22 | 1 |
| 2.4 mg/mL in PVC bag, 4 hr agitation | CL, CO, PFVP | 2.10 | 0.03 | 18.5 | 78.0 | 3.6 | 0.8 | 99.1 | 0.1 | 5.9 | 22 | 1 |
| 2.4 mg/mL in PVC bag, 6 hr agitation | CL, CO, PFVP | 2.05 | 0.01 | 18.6 | 78.2 | 3.3 | 0.8 | 99.1 | 0.1 | 5.9 | 10 | 0 |

CO = Colorless,
CL = Clear,
PFVP = Practically Free of Visible Particulates,
$A_{350}$ = absorbance at 350 nm The product tested in simulated administration studies as described above was physically and chemically stable under the tested conditions. Infusion bags, infusion sets, filters, and/or IV administration aids composed of different product-contacting materials are added upon successful qualification.

In addition to the static stability, an IV bag agitation study is performed with α-PDL1 formulated in 20 mM histidine acetate, 120 mM sucrose, pH 5.8 with 0.02% PS20, which is potentially the lowest PS20 level that could be observed in drug product over shelf life. The agitation is performed at 2-8° C. with orbital shaker at speed of 100 rpm. The data suggests that with 0.02% PS20 in drug product, α-PDL1 is stable upon agitation at 5° C. after diluting in IV bags (Table 16).

Sequences of the Antibody Used in the Examples

```
α-PDL1 Light Chain Variable Region
                                              (SEQ ID NO: 7)
DIQMTQSPSSLSASVGDRVTITCRASQDVSTAVAWYQQKPGKAPKLLIYSASFLYSGVPS

RFSGSGSGTDFTLTISSLQPEDFATYYCQQYLYHPATFGQGTKVEIKR

α-PDL1 Heavy Chain Variable Region
                                              (SEQ ID NO: 8)
EVQLVESGGGLVQPGGSLRLSCAASGFTFSDSWIHWVRQAPGKGLEWVAWISPYGGST

YYADSVKGRFTISADTSKNTAYLQMNSLRAEDTAVYYCARRHWPGGFDYWGQGTLVT

VSSASTK

α-PDL1 Full Light Chain
                                              (SEQ ID NO: 9)
DIQMTQSPSSLSASVGDRVTITCRASQDVSTAVAWYQQKPGKAPKLLIYSASFLYSGVPS

RFSGSGSGTDFTLTISSLQPEDFATYYCQQYLYHPATFGQGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC

α-PDL1 Full Heavy Chain
                                              (SEQ ID NO: 10)
EVQLVESGGGLVQPGGSLRLSCAASGFTFSDSWTHWVRQAPGKGLEWVAWISPYGGST

YYADSVKGRFTISADTSKNTAYLQMNSLRAEDTAVYYCARRHWPGGFDYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE
```

-continued

EQYASTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLT

VDKSRWQQGNVFSCSVMHEALHNHYTQKSLSLSPG

---

What is claimed is:

1. A stable aqueous pharmaceutical formulation, the formulation comprising an anti-programmed death ligand 1 (anti-PD-L1) monoclonal antibody in a concentration of 60 mg/ml, histidine acetate in a concentration of 20 mM, sucrose in a concentration of 120 mM, polysorbate 20 in a concentration of 0.04% (w/v), and pH 5.8; wherein said monoclonal antibody comprises a light chain variable region comprising the amino acid sequence of SEQ ID NO:7, and a heavy chain variable region comprising the amino acid sequence of SEQ ID NO:32.

2. The formulation of claim 1, wherein said monoclonal antibody is not subject to prior lyophilization.

3. The formulation of claim 1, wherein said monoclonal antibody is a full length antibody.

4. The formulation of claim 1, wherein said monoclonal antibody is an IgG1, an IgG2, an IgG3 or an IgG4 antibody.

5. The formulation of claim 1, wherein said monoclonal antibody is an antibody fragment comprising an antigen-binding region.

6. The formulation of claim 5, wherein the antibody fragment is a Fab or F(ab')$_2$ fragment.

7. The formulation of claim 1, wherein said monoclonal antibody is stored in a glass vial or a metal alloy container.

8. The formulation of claim 7, wherein the metal alloy is 316L stainless steel or hastelloy.

9. The formulation of claim 1, wherein the formulation is stable at 2-8° C. for at least 6 months.

10. The formulation of claim 9, wherein the antibody in the formulation retains at least about 80% of its biological activity after storage.

11. The formulation of claim 10, wherein the biological activity is measured by antibody binding to PD-L1.

12. The formulation of claim 1 which is sterile.

13. The formulation of claim 1 which is suitable to be administered to a subject.

14. The formulation of claim 1 which is for intravenous (IV) administration.

15. An article of manufacture comprising a container holding the stable aqueous pharmaceutical formulation of claim 1.

16. The article of claim 15, wherein the container is a glass vial or a metal alloy container.

17. The article of claim 16, wherein the metal alloy is 316L stainless steel or hastelloy.

18. The formulation of claim 1, wherein the monoclonal antibody is an IgG1 antibody and comprises a N297A substitution in the constant region, numbering of the residue is that of the EU index as in Kabat.

19. A stable aqueous pharmaceutical formulation, the formulation comprising an anti-PD-L1 monoclonal antibody in a concentration of 60 mg/ml, histidine acetate in a concentration of 20 mM, sucrose in a concentration of 120 mM, polysorbate 20 in a concentration of 0.04% (w/v), and pH 5.8; wherein said monoclonal antibody comprises a light chain comprising the amino acid sequence of SEQ ID NO:9, and a heavy chain comprising the amino acid sequence of SEQ ID NO:10.

20. The formulation of claim 19, wherein said monoclonal antibody is not subject to prior lyophilization.

21. The formulation of claim 19, wherein said monoclonal antibody is stored in a glass vial or a metal alloy container.

22. The formulation of claim 21, wherein the metal alloy is 316L stainless steel or hastelloy.

23. The formulation of claim 19, wherein the formulation is stable at 2-8° C. for at least 6 months.

24. The formulation of claim 23, wherein the antibody in the formulation retains at least about 80% of its biological activity after storage.

25. The formulation of claim 24, wherein the biological activity is measured by antibody binding to PD-L1.

26. The formulation of claim 19 which is sterile.

27. The formulation of claim 19 which is suitable to be administered to a subject.

28. The formulation of claim 19 which is for intravenous (IV) administration.

29. An article of manufacture comprising a container holding the stable aqueous pharmaceutical formulation of claim 19.

30. The article of claim 29, wherein the container is a glass vial or a metal alloy container.

31. The article of claim 30, wherein the metal alloy is 316L stainless steel or hastelloy.

* * * * *